(12) United States Patent
Okada et al.

(10) Patent No.: US 10,961,380 B2
(45) Date of Patent: Mar. 30, 2021

(54) THREE-DIMENSIONAL-FORMING PHOTO-CURABLE COMPOSITION, METHOD FOR PRODUCING THREE-DIMENSIONAL ARTICLE FROM THE PHOTO-CURABLE COMPOSITION, AND RESIN

(71) Applicant: CANON KABUSHIKI KAISHA, Tokyo (JP)

(72) Inventors: Seiji Okada, Kawasaki (JP); Kyohei Wada, Fuchu (JP)

(73) Assignee: Canon Kabushiki Kaisha, Tokyo (JP)

( * ) Notice: Subject to any disclaimer, the term of this patent is extended or adjusted under 35 U.S.C. 154(b) by 19 days.

(21) Appl. No.: 16/554,453

(22) Filed: Aug. 28, 2019

(65) Prior Publication Data

US 2019/0382576 A1 Dec. 19, 2019

Related U.S. Application Data

(63) Continuation of application No. PCT/JP2018/006708, filed on Feb. 23, 2018.

(30) Foreign Application Priority Data

Mar. 3, 2017 (JP) .............................. JP2017-040855
Jul. 19, 2017 (JP) .............................. JP2017-140151

(51) Int. Cl.
| | |
|---|---|
| *C08L 33/12* | (2006.01) |
| *B33Y 10/00* | (2015.01) |
| *B33Y 70/00* | (2020.01) |
| *A61K 6/893* | (2020.01) |
| *C08L 75/14* | (2006.01) |
| *C08G 83/00* | (2006.01) |

(52) U.S. Cl.
CPC ............ *C08L 33/12* (2013.01); *C08G 83/007* (2013.01); *A61K 6/893* (2020.01); *B33Y 10/00* (2014.12); *B33Y 70/00* (2014.12); *C08L 75/14* (2013.01)

(58) Field of Classification Search
CPC ........ C08F 2/50; C08F 301/00; C08F 290/00; C08F 222/102; C08F 220/1811; C08L 33/12; C08G 83/007; B33Y 10/00; B33Y 70/00
USPC ........................................................ 524/556
See application file for complete search history.

(56) References Cited

U.S. PATENT DOCUMENTS

2017/0333167 A1* 11/2017 Hagiwara ............. G03F 7/2012

FOREIGN PATENT DOCUMENTS

| JP | 2009-288518 A | 12/2009 |
|---|---|---|
| JP | 2016-167036 A | 9/2016 |
| JP | 2017-048288 A | 3/2017 |
| JP | 2018-039962 A | 3/2018 |
| WO | 2012/147745 A1 | 11/2012 |
| WO | 2015/200201 A1 | 12/2015 |
| WO | 2016/071811 A1 | 5/2016 |
| WO | 2017/154335 A1 | 9/2017 |

\* cited by examiner

*Primary Examiner* — William K Cheung
(74) *Attorney, Agent, or Firm* — Canon U.S.A., Inc., IP Division

(57) ABSTRACT

A three-dimensional-forming photo-curable composition includes a (meth)acrylic compound having a (meth)acryloyl group; a photo-radical generator; and a polyrotaxane having a plurality of cyclic molecules having at least one of a (meth)acryloyl group and a hydroxyl group.

8 Claims, 3 Drawing Sheets

(A)

(B)

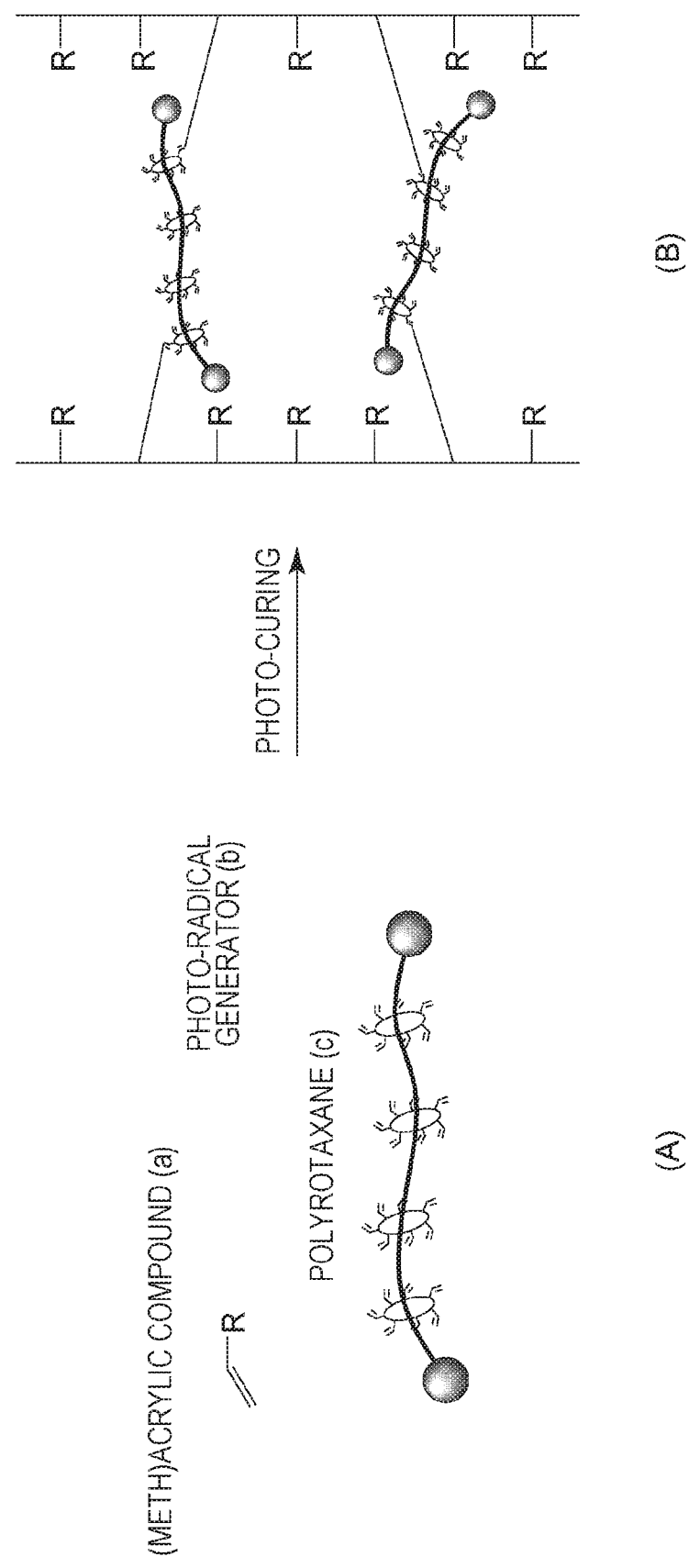

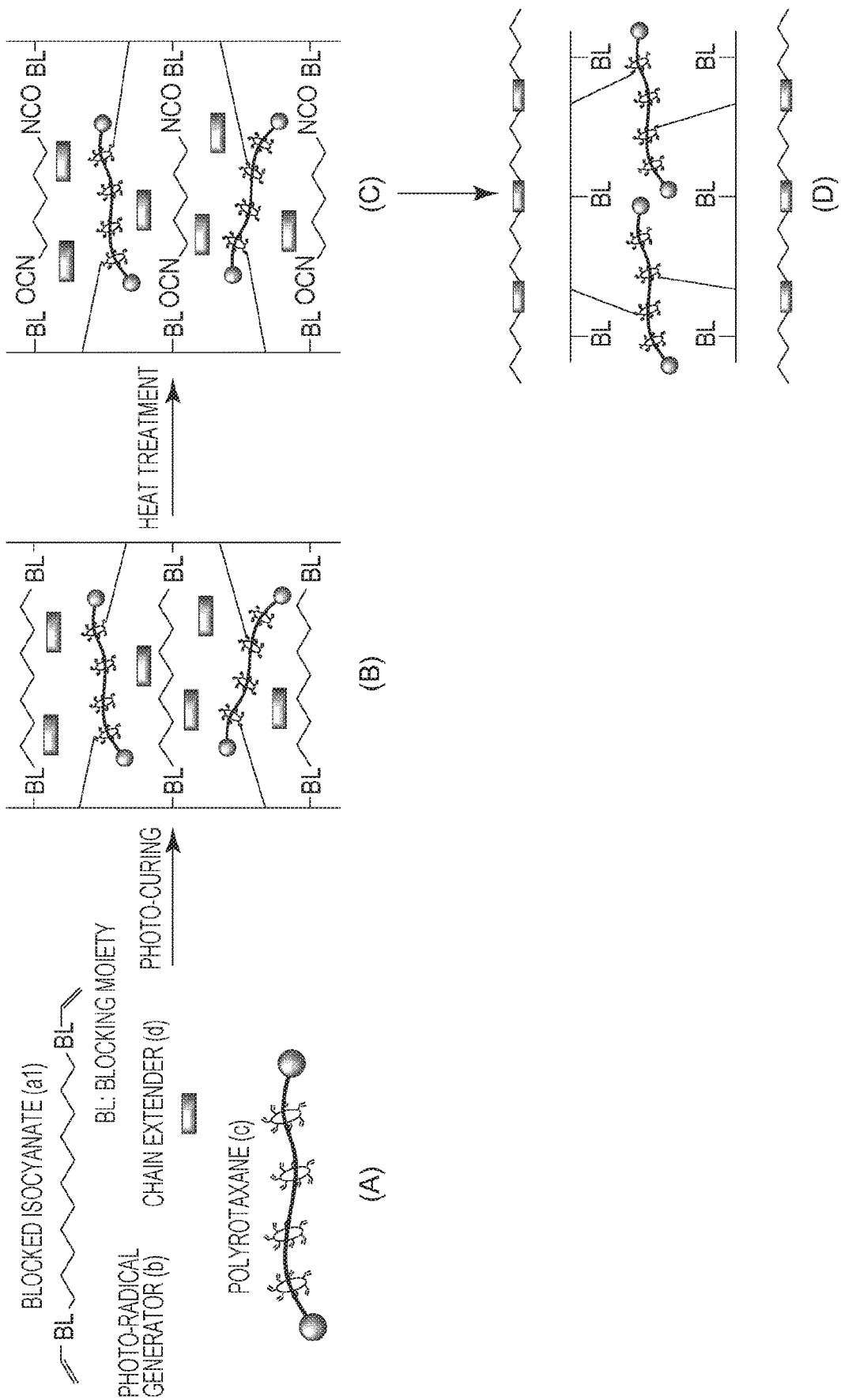

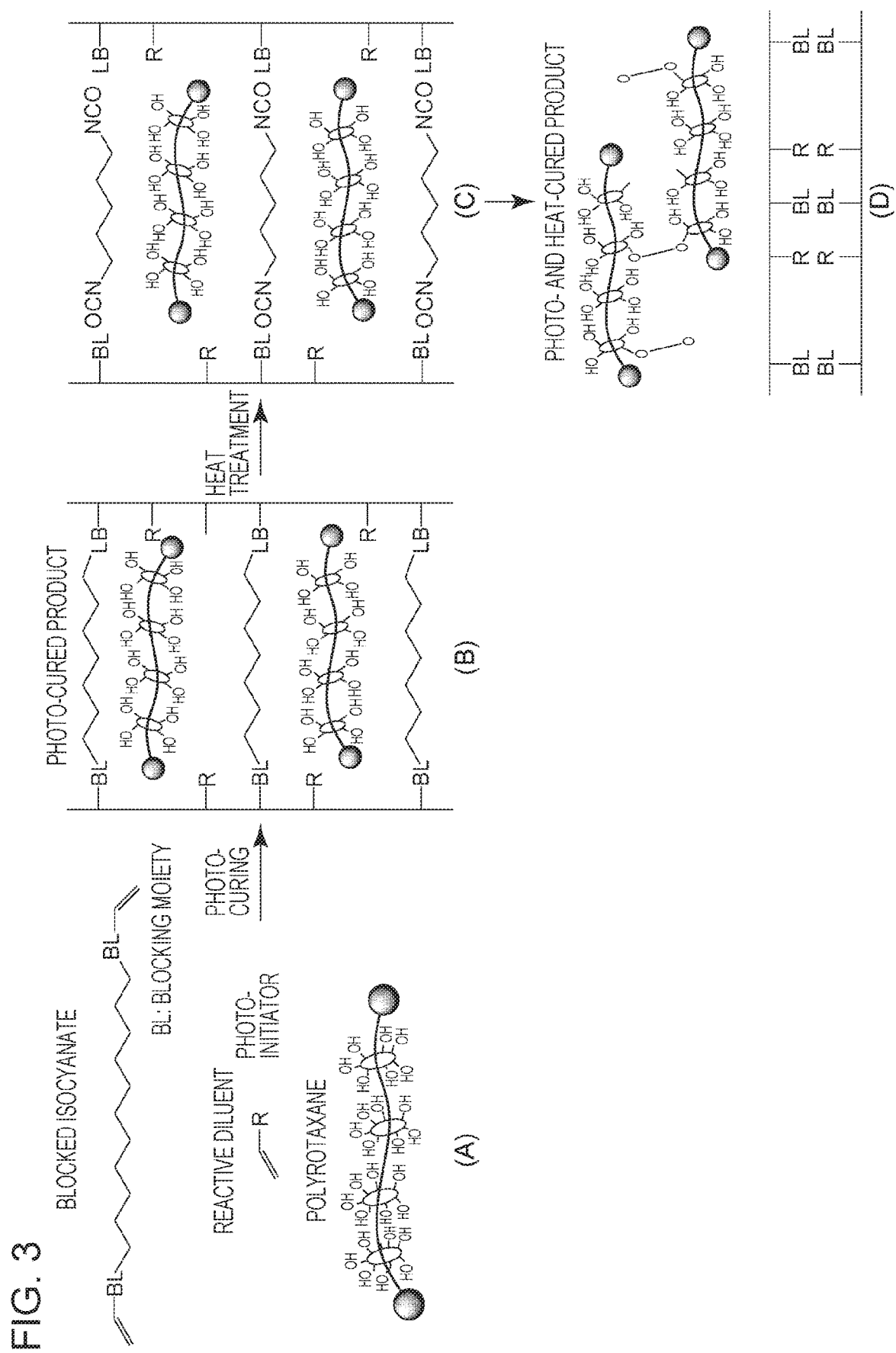

THREE-DIMENSIONAL-FORMING PHOTO-CURABLE COMPOSITION, METHOD FOR PRODUCING THREE-DIMENSIONAL ARTICLE FROM THE PHOTO-CURABLE COMPOSITION, AND RESIN

CROSS-REFERENCE TO RELATED APPLICATIONS

This application is a Continuation of International Patent Application No. PCT/JP2018/006708, filed Feb. 23, 2018, which claims the benefit of Japanese Patent Application No. 2017-040855, filed Mar. 3, 2017 and Japanese Patent Application No. 2017-140151, filed Jul. 19, 2017, all of which are hereby incorporated by reference herein in their entirety.

TECHNICAL FIELD

The present invention relates to a three-dimensional-forming photo-curable composition, a method for producing a three-dimensional article from the photo-curable composition, and a resin.

BACKGROUND ART

Thorough studies have been performed on optical three-dimensional-forming method (stereolithography), which is a process of curing a layer of a liquid photo-curable composition with light such as ultraviolet rays such that such layers are sequentially stacked to produce a desired three-dimensional article. Stereolithography, which is applied to formation of prototypes for checking the structures (rapid prototyping), has also come to be applied to, for example, formation of working models for checking the functions or formation of molds (rapid tooling). In addition, stereolithography has even come to be applied to formation of actual products (rapid manufacturing).

With such backgrounds, there has been a demand for better properties of three-dimensional-forming photo-curable compositions used for stereolithography. Recently, there has been a demand for a three-dimensional-forming photo-curable composition that has good mechanical characteristics (such as strength, rigidity, and toughness) comparable to those of versatile engineering plastics and that is used for forming three-dimensional articles.

Patent Literature 1 describes a method of subjecting a photo-curable composition containing a blocked isocyanate containing an acryloyl group and a chain extender to forming (photo-curing) by stereolithography, and further subjecting the resultant photo-cured product to heat treatment to form a three-dimensional article. This enables formation of three-dimensional articles that have high strength and rigidity, compared with existing photo-curable compositions, and enables formation of three-dimensional articles that are well-balanced in terms of strength, rigidity, and toughness.

CITATION LIST

Patent Literature

PTL 1 International Publication No. 2015/200201

In PTL 1, the photo-cured product is subjected to heat treatment to achieve a decrease in the crosslinking density and to generate polyurethane or polyurea to thereby provide improved toughness. However, the method described in PTL 1 does not provide cured products having sufficiently high toughness.

SUMMARY OF INVENTION

Accordingly, in order to address such a problem, an object of the present invention is to provide a three-dimensional-forming photo-curable composition that enables formation of a three-dimensional article having higher toughness than before.

A three-dimensional-forming photo-curable composition according to an aspect of the present invention includes a (meth)acrylic compound having a (meth)acryloyl group; a photo-radical generator; and a polyrotaxane having a plurality of cyclic molecules having at least one of a (meth)acryloyl group and a hydroxyl group.

Further features of the present invention will become apparent from the following description of exemplary embodiments with reference to the attached drawings.

BRIEF DESCRIPTION OF DRAWINGS

FIG. 1 is a schematic view illustrating a reaction scheme of, by irradiation with light, curing a photo-curable composition according to a first embodiment.

FIG. 2 is a schematic view illustrating a reaction scheme of, by irradiation with light, curing a photo-curable composition including a polyrotaxane having a (meth)acryloyl group according to a second embodiment.

FIG. 3 is a schematic view illustrating a reaction scheme of, by irradiation with light, curing a photo-curable composition including a polyrotaxane having a hydroxyl group according to a second embodiment.

DESCRIPTION OF EMBODIMENTS

Hereinafter, embodiments according to the present invention will be described. However, the present invention is not limited to the following embodiments. Embodiments provided by, for example, appropriately changing or improving the following embodiments without deviation from the spirit and scope of the present invention and on the basis of ordinary knowledge of those skilled in the art, are also encompassed in the scope of the present invention.

First Embodiment

A three-dimensional-forming photo-curable composition (hereafter, also simply referred to as the "photo-curable composition") according to this embodiment includes a (meth)acrylic compound (a) as a polymerizable compound, a photo-radical generator (b), and a polyrotaxane (c).

Hereinafter, components of the photo-curable composition according to this embodiment will be described in detail.

(Meth)Acrylic Compound (a)

The (meth)acrylic compound (a) is a compound that has at least one (meth)acryloyl group and is polymerized by a radical generated from the photo-radical generator (b) described later.

In this Specification, the "(meth)acryloyl group" means an acryloyl group or a methacryloyl group; and the "(meth) acrylic compound" means an acrylic compound or a methacrylic compound.

The (meth)acrylic compound (a) may be constituted by a single (meth)acrylic compound species alone, or may be constituted by a plurality of (meth)acrylic compound species.

The number of (meth)acryloyl groups of the (meth)acrylic compound (a) is not particularly limited. Non-limiting examples of the (meth)acrylic compound (a) include a monofunctional (meth)acrylic compound intramolecularly having a single (meth)acryloyl group, a bifunctional (meth)acrylic compound intramolecularly having two (meth)acryloyl groups, a trifunctional (meth)acrylic compound intramolecularly having three (meth)acryloyl groups, and a four- or higher functional (meth)acrylic compound intramolecularly having four or more (meth)acryloyl groups.

The (meth)acrylic compound (a) may be, for example, a urethane (meth)acrylic compound having a urethane structure in the molecular structure, or a polyester (meth)acrylic compound having a polyester structure in the molecular structure.

Non-limiting specific examples of the (meth)acrylic compound (a) include monofunctional (meth)acrylic compounds such as methyl (meth)acrylate, ethyl (meth)acrylate, n-propyl (meth)acrylate, isopropyl (meth)acrylate, n-butyl (meth)acrylate, isobutyl (meth)acrylate, tert-butyl (meth)acrylate, n-pentyl (meth)acrylate, n-hexyl (meth)acrylate, cyclohexyl (meth)acrylate, n-heptyl (meth)acrylate, n-octyl (meth)acrylate, isooctyl (meth)acrylate, 2-ethylhexyl (meth)acrylate, nonyl (meth)acrylate, isononyl (meth)acrylate, decyl (meth)acrylate, isodecyl (meth)acrylate, dodecyl (meth)acrylate, lauryl (meth)acrylate, stearyl (meth)acrylate, tridecyl (meth)acrylate, tridecyl (meth)acrylate, cyclohexyl (meth)acrylate, isobornyl (meth)acrylate, dicyclopentanyl (meth)acrylate, adamantyl (meth)acrylate, phenyl (meth)acrylate, toluyl (meth)acrylate, benzyl (meth)acrylate, 2-methoxyethyl (meth)acrylate, 3-methoxybutyl (meth)acrylate, 2-hydroxyethyl (meth)acrylate, 2-hydroxypropyl (meth)acrylate, and stearyl (meth)acrylate; bifunctional (meth)acrylic compounds such as 1,4-butanediol di(meth)acrylate, 1,6-hexanediol di(meth)acrylate, 1,9-nonanediol di(meth)acrylate, tricyclodecanedimethanol (meth)acrylate, bisphenol A (poly)ethoxy di(meth)acrylate, bisphenol A (poly)propoxy di(meth)acrylate, bisphenol F (poly)ethoxy di(meth)acrylate, and ethylene glycol di(meth)acrylate; trifunctional (meth)acrylic compounds such as trimethylolpropane tri(meth)acrylate, trimethyloloctane tri(meth)acrylate, trimethylolpropane polyethoxy tri(meth)acrylate, trimethylolpropane (poly)propoxy tri(meth)acrylate, trimethylolpropane (poly)ethoxy (poly)propoxy tri(meth)acrylate, pentaerythritol tri(meth)acrylate, tris[(meth)acryloyloxyethyl] isocyanurate, and caprolactone-modified tris[(meth)acryloyloxyethyl] isocyanurate; and four- or higher functional (meth)acrylic compounds such as ditrimethylolpropane tetra(meth)acrylate, pentaerythritol polyethoxy tetra(meth)acrylate, pentaerythritol polyethoxy tetra(meth)acrylate, pentaerythritol (poly)propoxy tetra(meth)acrylate, pentaerythritol tetra(meth)acrylate, dipentaerythritol tetra(meth)acrylate, dipentaerythritol penta(meth)acrylate, and dipentaerythritol hexa(meth)acrylate.

Non-limiting specific examples of the urethane (meth)acrylic compound include polycarbonate-based urethane (meth)acrylate, polyester-based urethane (meth)acrylate, polyether-based urethane (meth)acrylate, and caprolactone-based urethane (meth)acrylate.

Such a urethane (meth)acrylic compound can be obtained by causing a reaction between a polyol and a diisocyanate to provide an isocyanate compound, and causing a reaction between the isocyanate compound and a (meth)acrylate monomer having a hydroxyl group. Specific examples of the polyol include polycarbonate polyol, polyester polyol, polyether polyol, and polycaprolactone polyol.

The polyester (meth)acrylic compound is obtained by, for example, causing condensation between a polycarboxylic acid and a polyol to provide a polyester oligomer having hydroxyl groups at both ends, and subsequently esterifying the hydroxyl groups at both ends with acrylic acid.

Photo-Radical Generator (b)

The photo-radical generator (b) is a compound that generates a radical serving as a polymerization factor upon exposure to an active energy ray such as light of a predetermined wavelength, to initiate a polymerization reaction. The photo-radical agent (b) may be a compound that is decomposed upon exposure to an active energy ray to generate a radical. Specific examples of the active energy ray include infrared rays, visible light, ultraviolet rays, far-ultraviolet rays, X-rays, charged particle beams such as electron beams, and radiation.

Non-limiting specific examples of the photo-radical generator (b) include carbonyl compounds such as benzoin, benzoin monomethyl ether, benzoin isopropyl ether, acetoin, benzil, benzophenone, p-methoxybenzophenone, diethoxyacetophenone, benzil dimethyl ketal, 2,2-diethoxyacetophenone, 1-hydroxycyclohexyl phenyl ketone, methylphenyl glyoxylate, ethylphenyl glyoxylate, and 2-hydroxy-2-methyl-1-phenylpropan-1-one; sulfur compounds such as tetramethylthiuram monosulfide and tetramethylthiuram disulfide; and acylphosphine oxides such as 2,4,6-trimethylbenzoyldiphenylphosphine oxide.

Non-limiting examples of commercially available products of the photo-radical generator include IRGACURE (registered trademark) series such as IRGACURE 184 and IRGACURE 819, DAROCUR (registered trademark) series such as DAROCUR 1173 and DAROCUR TPO (all manufactured by BASF); and KAYACURE (registered trademark) series such as KAYACURE DETX-S and KAYACURE CTX (all manufactured by Nippon Kayaku Co., Ltd.).

The amount of photo-radical generator (b) added relative to the total amount (100 mass %) of the photo-curable composition is preferably 0.05 mass % or more and 20 mass % or less, more preferably 0.1 mass % or more and 5 mass % or less. When the addition amount is less than 0.05 mass %, the amount of radical generated is insufficient and the photo-curable composition exhibits a lower polymerization conversion, so that a three-dimensional article obtained by photo-curing and subsequently heat-treating the photo-curable composition has insufficient strength. When the addition amount is more than 30 mass %, most of light radiated to the photo-curable composition may be absorbed by the photo-radical generator (b) present in the excessive amount, so that light may not reach inside of the curable composition. Thus, the inner photo-curable composition of the photo-curable composition may exhibit a lower polymerization conversion.

Polyrotaxane (c)

The polyrotaxane (c) is a supermolecule having a plurality of cyclic molecules having at least one functional group selected from a (meth)acryloyl group and a hydroxyl group, a linear molecule penetrating and skewering the plurality of cyclic molecules, and blocking groups disposed at both ends of the linear molecule to prevent the cyclic molecules from leaving. In the polyrotaxane (c), the cyclic molecules are freely movable like pulleys along the linear molecule chain. The polyrotaxane (c) has the following structure: the cyclic molecules are blocked at the ends of the linear molecule by the blocking groups, so that the cyclic molecules cannot leave from the linear molecule.

Cyclic Molecules of Polyrotaxane

Such a cyclic molecule of polyrotaxane is not particularly limited as long as it has at least one functional group selected from a (meth)acryloyl group and a hydroxyl group, surrounds a linear molecule, and is freely movable like a pulley along the linear molecule chain. Incidentally, the cyclic molecule does not necessarily have a completely closed ring shape, and may have a substantially "C" shape, for example.

Non-limiting specific examples of the cyclic molecules of the polyrotaxane include cyclodextrins such as α-cyclodextrin, β-cyclodextrin, and γ-cyclodextrin; crown ethers, benzocrowns, dibenzocrowns, and dicyclohexanocrowns. Of these, preferred are cyclodextrins because they are easily available and an appropriate ring size is easily selected. In particular, the cyclic molecules of the polyrotaxane are more preferably α-cyclodextrin. Alternatively, the polyrotaxane (c) may include, in a single polyrotaxane molecule, two or more different cyclic molecule species.

Such a cyclic molecule of the polyrotaxane has at least one functional group selected from a (meth)acryloyl group and a hydroxyl group, and may have two or more (meth) acryloyl groups and/or two or more hydroxyl groups. When the polyrotaxane (c) includes, in a single polyrotaxane molecule, two or more different cyclic molecule species, at least one cyclic molecule species has at least one (meth) acryloyl group or hydroxyl group.

Linear Molecule of Polyrotaxane

The linear molecule of the polyrotaxane is not particularly limited as long as it is a molecule or substance that is surrounded by cyclic molecules so as to be integrated with the cyclic molecules without covalent bonds, and that is linear.

In this Specification, "linear" means being substantially "linear". Specifically, as long as the cyclic molecules are slidable or movable along the linear molecule, the linear molecule may have a branched chain; and, as long as the cyclic molecules are slidable or movable along the linear molecule, the linear molecule may be bent or helical. The length of the "linear" is not particularly limited as long as the cyclic molecules are slidable or movable along the linear molecule.

Non-limiting specific examples of the linear molecule of the polyrotaxane include polyesters such as polyalkylenes and polycaprolactone; polyethers such as polyalkylene glycols such as polyethylene glycol and polypropylene glycol; polyamides, polyacrylics, and linear molecules having benzene rings. Of these, from the viewpoint of ease of being surrounded by molecules and flexibility, preferred are polyethers, in particular, more preferred is polyethylene glycol.

The linear molecule of the polyrotaxane preferably has a number-average molecular weight of 1,000 or more and 1,000,000 or less, more preferably 5,000 or more and 50,000 or less. When the linear molecule has a molecular weight of less than 1,000, the cyclic molecules do not sufficiently provide the pulley effect, so that impact properties are not sufficiently improved. When the molecular weight is more than 1,000,000, an optical three-dimensional-forming photo-curable resin composition according to the present invention may have an excessively high viscosity, so that it may not be formed using a stereolithography machine.

Blocking Groups

The blocking groups are disposed at the ends (both ends) of the linear molecule of the polyrotaxane to play the role of preventing the cyclic molecules from leaving from the linear molecule. The blocking groups are not particularly limited in terms of structure as long as they play the role of stoppers for preventing the cyclic molecules from leaving. The method for preventing the leaving may be a method of using bulky groups to physically prevent the leaving, or a method of using ionic groups to electrically prevent the leaving.

Non-limiting specific examples of the blocking groups include adamantane groups, dinitrophenyl groups, cyclodextrins, trityl groups, fluoresceins, pyrenes, and derivatives or modified groups of the foregoing.

Examples of commercially available products of polyrotaxane usable as the polyrotaxane (c) having a (meth) acryloyl group according to this embodiment include SeRM SM3405P, SeRM SA3405P, SeRM SM3400C, SeRM SA3400C, and SeRM SA2400C (all manufactured by Advanced Softmaterials Inc.). Examples of commercially available products of the polyrotaxane (c) having a hydroxyl group include SeRM SH3400P, SeRM SH2400P, and SeRM SH1300P (all manufactured by Advanced Softmaterials Inc.).

The mixing ratio of the polyrotaxane (c) is not particularly limited as long as advantages of the present invention are not degraded. For example, the mixing ratio relative to the total amount (100 mass %) of the photo-curable composition is preferably 1 mass % or more and 50 mass % or less, more preferably 5 mass % or more and 30 mass % or less. When the mixing ratio is less than 1 mass %, the photo-curable composition may be cured to provide a cured product having lower toughness. When the mixing ratio is more than 50 mass %, the photo-curable composition may be cured to provide a cured product having a lower elastic modulus or lower strength.

Other Components

Radical Polymerizable Compound

The photo-curable composition according to this embodiment may include, in addition to the (meth)acrylic compound, another radical polymerizable compound. Non-limiting examples of the radical polymerizable compound include styrene-based monomers, styrene-based oligomers, acrylonitrile compounds, vinyl ester-based monomers, vinyl ester-based oligomers, N-vinylpyrrolidone, acrylamide-based monomers, acrylamide-based oligomers, conjugated diene-based monomers, conjugated diene-based oligomers, vinyl ketone-based monomers, vinyl ketone-based oligomers, halogenated vinyl-based monomers, halogenated vinyl-based oligomers, halogenated vinylidene-based monomers, and halogenated vinylidene-based oligomers.

Cationic Polymerizable Compound

The photo-curable composition according to this embodiment may further include a cationic polymerizable compound. The cationic polymerizable compound is polymerized with acid generated from a photo-acid generator described later.

Non-limiting examples of the cationic polymerizable compound include epoxy-based monomers, epoxy-based oligomers, oxetane-based monomers, oxetane-based oligomers, vinyl ether-based monomers, and vinyl ether-based oligomers.

Photo-Acid Generator

When the photo-curable composition according to this embodiment includes the above-described cationic polymerizable compound, it may further include a photo-acid generator. The photo-acid generator is a compound that generates acid serving as a polymerization factor upon exposure to an active energy ray such as light of a predetermined wavelength, to initiate a polymerization reaction.

Non-limiting specific examples of the photo-acid generator include trichloromethyl-s-triazines, sulfonium salts, iodonium salts, quaternary ammonium salts, diazomethane compounds, imidosulfonate compounds, and oxime-sulfonate compounds.

When the photo-acid generator is included, the amount of photo-acid generator added relative to the total amount (100 mass %) of photo-curable composition is preferably 0.05 mass % or more and 20 mass % or less, more preferably 0.1 mass % or more and 5 mass % or less. When the addition amount is less than 0.05 mass %, the amount of acid generated is insufficient, the photo-curable composition exhibits a lower polymerization conversion, so that a three-dimensional article obtained by photo-curing and subsequently heat-treating the photo-curable composition has insufficient strength. When the addition amount is more than 30 mass %, most of light radiated to the photo-curable composition may be absorbed by the photo-acid generator present in the excessive amount, so that light may not reach inside of the curable composition. Thus, the inner photo-curable composition of the photo-curable composition may exhibit a lower polymerization conversion.

Reaction Accelerator

In the case of employing, as the chain extender (d), a compound having a hydroxyl group or in the case of using the polyrotaxane (c) having a hydroxyl group, a reaction accelerator is preferably added. The reaction accelerator is a compound that accelerates a reaction between a hydroxyl group and an isocyanate group provided by deblocking of the blocked isocyanate group of a blocked isocyanate (a1) or a blocked isocyanate (a3) described later. Examples of the reaction accelerator include tin compounds such as dibutyltin dilaurate, dioctyltin dilaurate, and dibutyltin dioctanoate.

Such reaction accelerators (e) may be used alone or in combination of two or more thereof. The amount of reaction accelerator (e) used relative to the total amount (100 mass %) of polyol is preferably 0.001 mass % or more and 10 mass % or less.

Other Additives

The photo-curable composition according to this embodiment may optionally include, as long as advantages of the present invention are not degraded, an appropriate amount of one or two or more additives: a reactive diluent, a coloring agent such as a pigment or a dye, a defoaming agent, a leveling agent, a thickener, a flame retardant, an antioxidant, an inorganic filler (such as crosslinked polymer particles, silica, a glass powder, a ceramic powder, or a metal powder), or a resin for modification (such as a thermoplastic resin, thermoplastic resin particles, or rubber particles).

The photo-curable composition according to this embodiment may include, in addition to the photo-radical generator (b), optionally appropriately an auxiliary photo-initiator or a sensitizer. Examples of the auxiliary photo-initiator or the sensitizer include benzoin compounds, acetophenone compounds, anthraquinone compounds, thioxanthone compounds, ketal compounds, benzophenone compounds, tertiary amine compounds, and xanthone compounds.

Functions of Three-Dimensional-Forming Photo-Curable Composition

The three-dimensional-forming photo-curable composition including the (meth)acrylic compound (a) and the photo-radical generator (b) is cured upon irradiation with light to form a cured product (three-dimensional article). At this time, a radical generated from the photo-radical generator (b) initiates the radical polymerization reaction of the (meth)acrylic compound (a) to cause curing of the photo-curable composition. In this case, in order to provide a cured product (three-dimensional article) having higher rigidity, the cured product (three-dimensional article) preferably has a high crosslinking density. However, existing three-dimensional-forming photo-curable compositions provide cured products in which crosslinking points do not move; for this reason, an excessively high crosslinking density results in low toughness and brittleness.

By contrast, the three-dimensional-forming photo-curable composition according to this embodiment includes the above-described polyrotaxane (c). In the polyrotaxane (c) according to this embodiment, the cyclic molecules in the polyrotaxane (c) include at least one functional group selected from a (meth)acryloyl group and a hydroxyl group.

When the cyclic molecules in the polyrotaxane (c) according to this embodiment include a (meth)acryloyl group, irradiating the photo-curable composition according to this embodiment with light causes a polymerization reaction within the (meth)acrylic compound (a), and additionally causes a polymerization reaction between the (meth)acrylic compound (a) and the polyrotaxane (c), and a polymerization reaction within the polyrotaxane (c). This provides a cured product (three-dimensional article) having a structure schematically illustrated in FIG. 1(B). Since the cyclic molecules in the polyrotaxane (c) are freely movable along the linear molecule chain of the polyrotaxane (c), some crosslinking points in the cured product are movable. In other words, under application of an external stress or the like, the crosslinking points move in accordance with the stress. Thus, in response to the stress, the tension among the polymers becomes uniform, so that the resultant cured product has high toughness, compared with existing photo-curable compositions.

When the cyclic molecules in the polyrotaxane (c) according to this embodiment include a hydroxyl group, irradiating the photo-curable composition according to this embodiment with light causes a polymerization reaction within the (meth)acrylic compound (a). This provides a cured product in which (meth)acryloyl groups and hydroxyl groups in the polyrotaxane (c) are bonded via hydrogen bonds in the resultant formed article. A post treatment of heating eliminates the internal stress caused during the curing: crosslinking points in the cured product move, so that the (meth)acryloyl groups and the polyrotaxane (c) become optimally disposed. Under application of an external stress or the like, the (meth)acryloyl groups in the formed article propagate the stress via the hydrogen bonds to the hydroxyl groups of the cyclic molecules of the polyrotaxane (c). Since the cyclic molecules of the polyrotaxane (c) are movable, in response to the stress, the tension among the polymers becomes uniform. As a result, as in the case where the cyclic molecules in the polyrotaxane (c) have a (meth)acryloyl group, the effect of the polyrotaxane provides a cured product that has high toughness, compared with existing photo-curable compositions.

Method for Producing Three-Dimensional Article

The photo-curable composition according to this embodiment is suitably applicable to a method for producing a three-dimensional article by an optical three-dimensional-forming method (stereolithography). Hereinafter, the method for producing a three-dimensional article from the photo-curable composition according to this embodiment will be described.

The stereolithography may be performed by a publicly known method. Specifically, the method for producing a three-dimensional article according to this embodiment includes a step of selectively irradiating the photo-curable composition according to this embodiment with an active energy ray such as light to cure a layer of the photo-curable composition; and this step is repeated to produce a three-dimensional article.

In the steps of curing a layer of the photo-curable composition, the photo-curable composition is selectively irradiated with an active energy ray on the basis of slice data of a target three-dimensional article.

The active energy ray radiated to the photo-curable composition is not particularly limited as long as the active energy ray cures the photo-curable composition according to this embodiment. Specific examples of the active energy ray include electromagnetic waves such as ultraviolet rays, visible light, infrared rays, X-rays, γ-rays, and laser beams; and corpuscular beams such as α-rays, β-rays, and electron beams. Of these, from the viewpoint of the absorption wavelength of the photo-radical generator (c) employed and equipment installation costs, ultraviolet rays are most preferred. The dose is not particularly limited, but is preferably 0.001 J/cm² or more and 10 J/cm² or less. When the dose is less than 0.001 J/cm², the photo-curable composition may not be sufficiently cured. When the dose is more than 10 J/cm², the irradiation time becomes long, which results in lower productivity.

The method of irradiating the photo-curable composition with an active energy ray is not particularly limited. For example, when light is radiated as the active energy ray, the following methods may be employed. The first method may be a method of using focused point light such as a laser beam, and two-dimensionally scanning this light over the photo-curable composition. In this case, the two-dimensional scanning may be performed by dot-by-dot scanning or line-by-line scanning. The second method may be an area exposure process of radiating light using a projector or the like in accordance with the shape of slice data. In this case, an active energy ray may be radiated to an area through an area scanning mask including a plurality of microoptical shutters arranged, such as liquid crystal shutters or digital micro mirror shutters.

In this step, after a formed article is obtained by stereolithography, the surface of the obtained formed article may be washed with a washing agent such as an organic solvent. The obtained formed article may be subjected to post-curing of radiating light or heat to cure unreacted residual components that may remain in the surface or inside of the formed article.

Second Embodiment

The photo-curable composition according to this embodiment includes, as the polymerizable compound (a) in the first embodiment, a blocked isocyanate (a1) having a (meth)acryloyl group described later. Specifically, the photo-curable composition according to the second embodiment includes, in the case where the polyrotaxane (c) has a (meth)acryloyl group, the blocked isocyanate (a1) having a (meth)acryloyl group, the photo-radical generator (b), and the chain extender (d); or the photo-curable composition according to the second embodiment includes, in the case where the polyrotaxane (c) has a hydroxyl group, the blocked isocyanate (a1) having a (meth)acryloyl group, the photo-radical generator (b), and the reaction accelerator (e).

Hereinafter, components of the photo-curable composition according to this embodiment will be described in detail. Incidentally, in the following description, the same explanations as in the first embodiment may be omitted.
Blocked isocyanate (a1)

The blocked isocyanate (a1) is represented by the following general formula (1).

(in the formula (1), A and C each independently represent a group represented by the following formula (2); and B represents a group represented by the following formula (3).

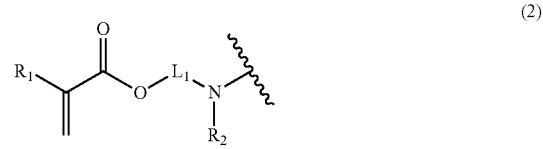

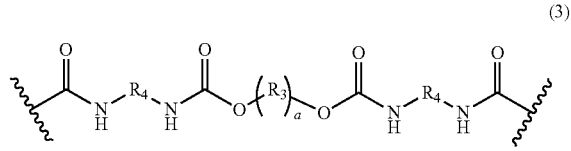

In the formula (2), $R_1$ represents a hydrogen atom or a methyl group, $R_2$ represents a hydrocarbon group that has 1 to 10 carbon atoms and may have a substituent, and $L_1$ represents a divalent hydrocarbon group that has 1 to 10 carbon atoms and may have a substituent. In the formula (3), $R_3$ and $R_4$ each independently represent a hydrocarbon group that has 1 to 20 carbon atoms and may have a substituent, and a is an integer of 1 or more and 100 or less.)

In the formula (2) and formula (3), when any one of $L_1$, $R_2$, $R_3$, and $R_4$ has a substituent, the substituent may be a substituent including a carbon atom. However, in this case, the substituent bonds to a non-carbon atom of $L_1$, $R_2$, $R_3$, or $R_4$. In this case, the number of carbon atoms of the substituent is not included in the number of carbon atoms of the "hydrocarbon group". The substituent may include a hetero atom.

As described above, the blocked isocyanate (a1) is a (meth)acrylic compound that includes at least two (meth)acryloyl groups.

In the formula (2), $R_2$ is preferably a group selected from a tert-butyl group, a tert-pentyl group, and a tert-hexyl group. This is preferable because it provides a decrease in the temperature of deblocking (deblocking temperature) during heat treatment of the photo-cured photo-curable composition. When $R_2$ is any one of the above-described groups, the blocked isocyanate (a1) is easily synthesized. When $R_2$ is any one of the above-described groups, the blocked isocyanate (a1) is synthesized at low costs.

In the formula (2), $L_1$ is preferably, from the viewpoint of ease of availability and ease of synthesis, an ethylene group or a propylene group.

In the formula (3), $R_3$ preferably has, from the viewpoint of ease of availability and ease of synthesis, at least one divalent linking group selected from the group consisting of the following formulas (A-1) to (A-4).

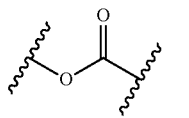
(A-3)

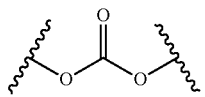
(A-4)

In the formula (A-1), c is an integer of 1 or more and 10 or less. In the formula (A-2), d is an integer of 1 or more and 10 or less.

In the formula (3), $R_3$ preferably has a group represented by the formula (A-4) above. This provides, by curing, a cured product having a higher elastic modulus.

In the formula (1), A and C are preferably the same. In other words, the blocked isocyanate (a1) is preferably represented by the following general formula (4). In this case, the blocked isocyanate (a1) is synthesized inexpensively and easily.

A-B-A  (4)

(in the formula (4), A represents a group represented by the formula (2) above, and B represents a group represented by the formula (3) above.)

Examples of the specific structure of the blocked isocyanate (a1) include the following structures.

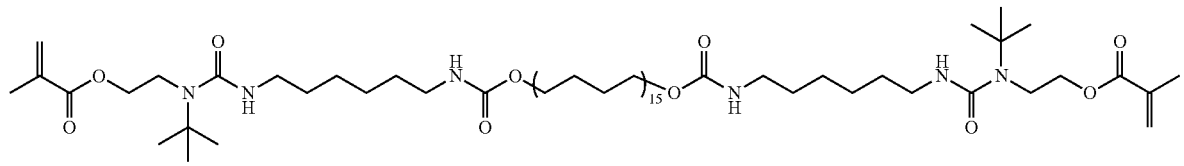
(X-1)

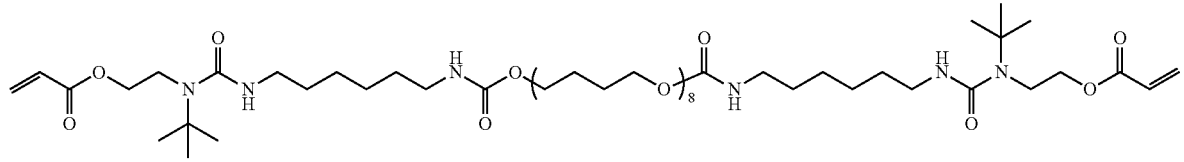
(X-2)

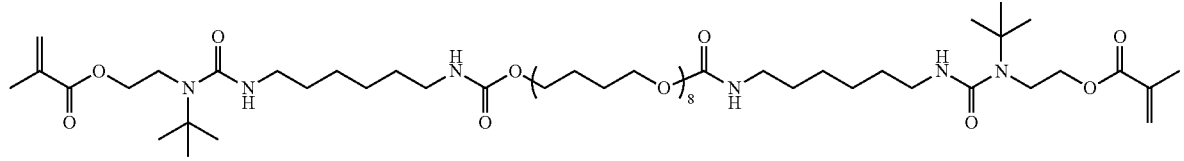
(X-3)

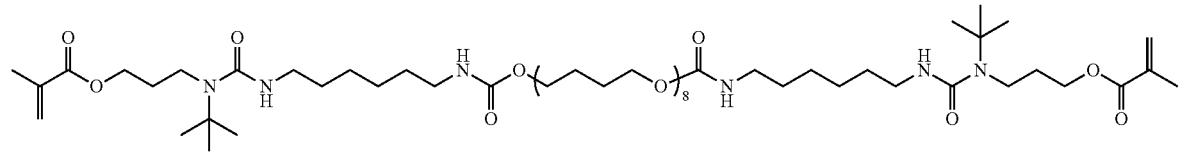
(X-4)

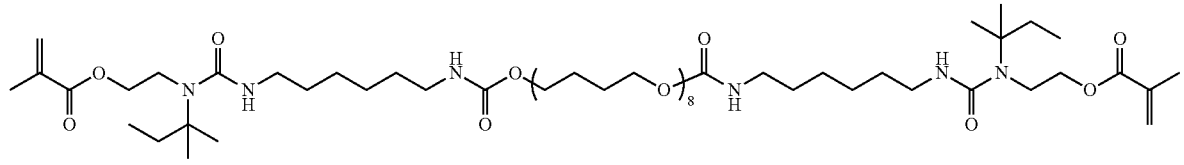
(X-5)

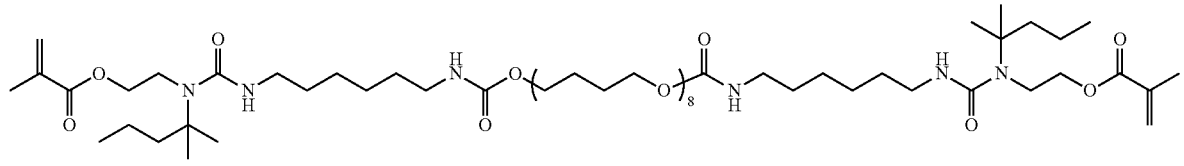
(X-6)

(X-7)
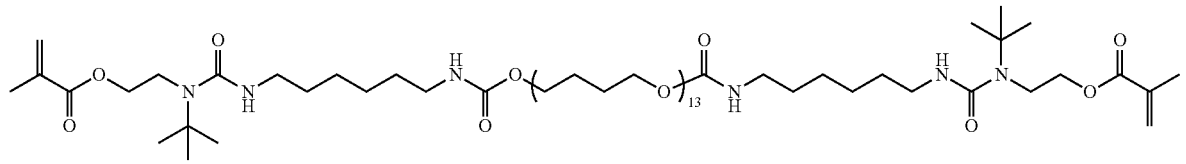
(X-8)
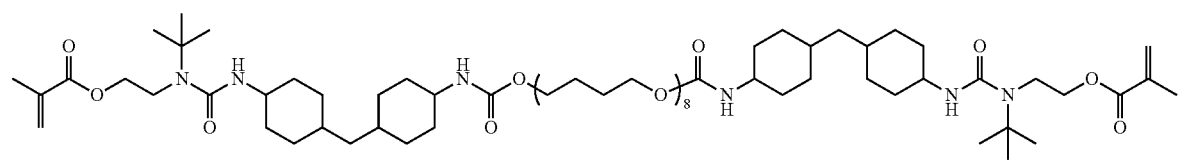
(X-9)
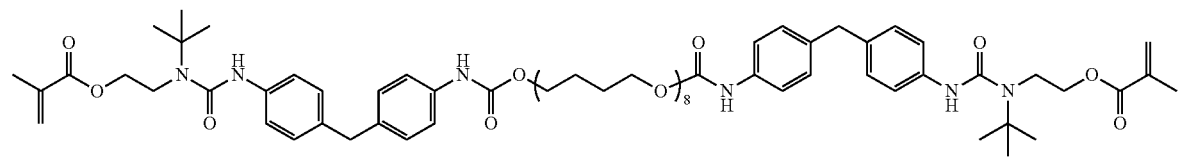
(X-10)
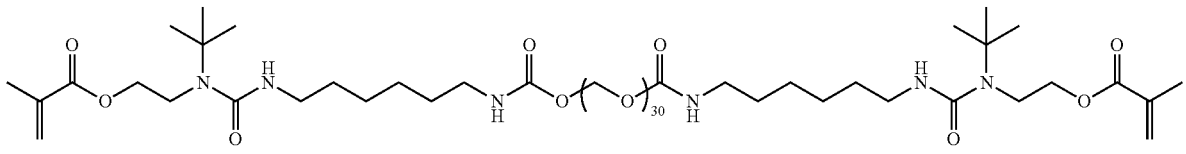
(X-12)
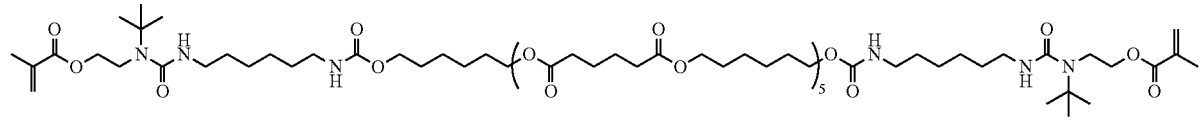
(X-13)
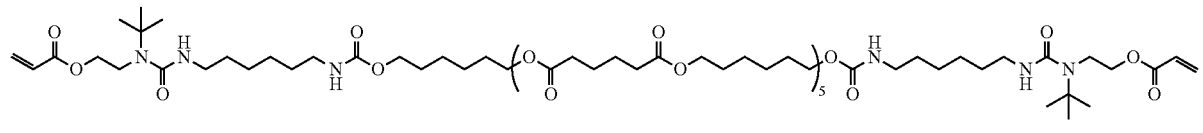
(X-14)
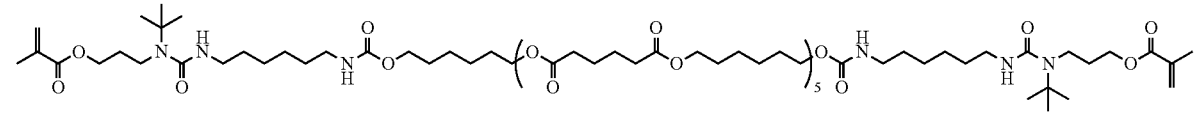
(X-15)
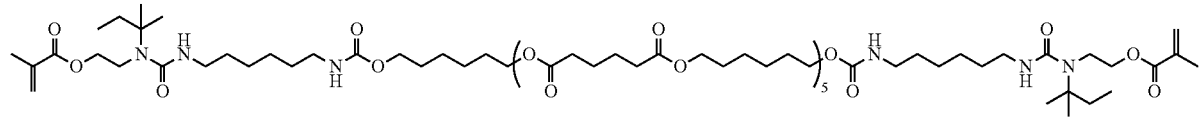
(X-16)
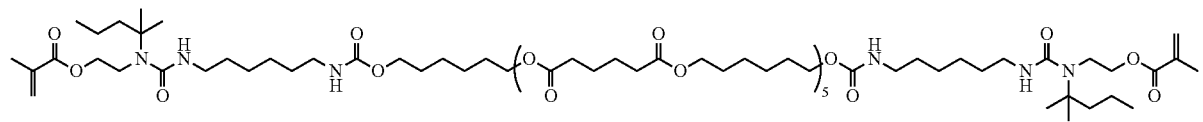

-continued

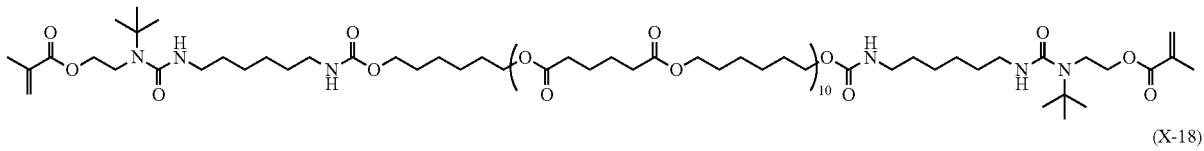

(X-17)

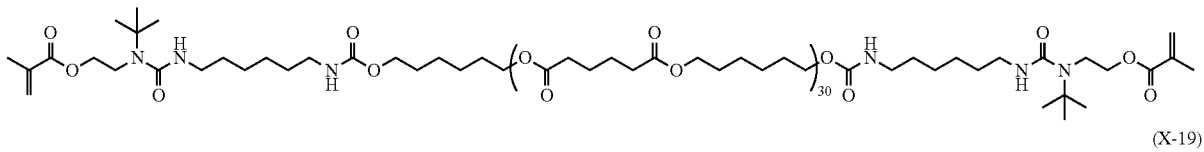

(X-18)

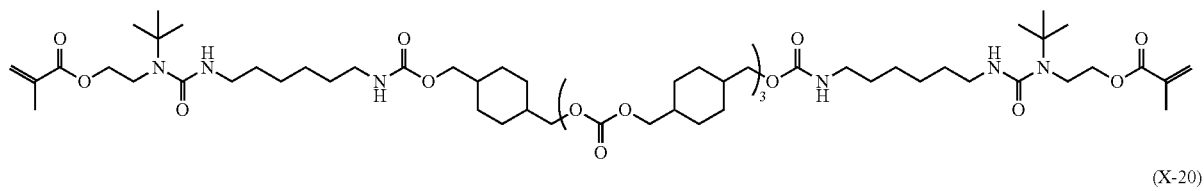

(X-19)

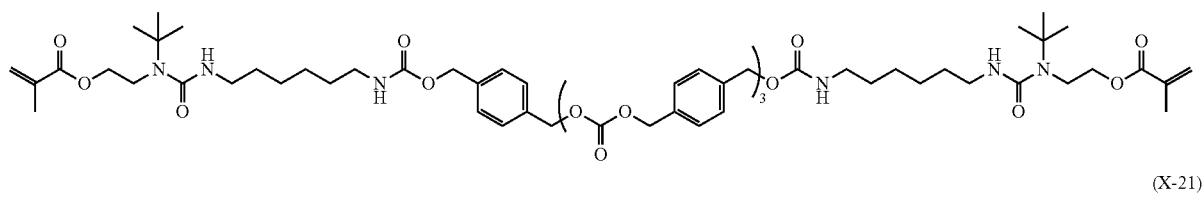

(X-20)

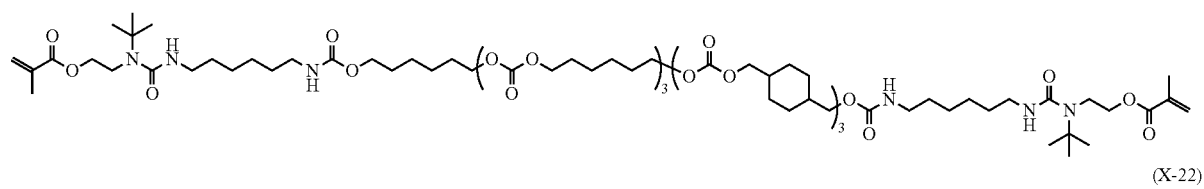

(X-21)

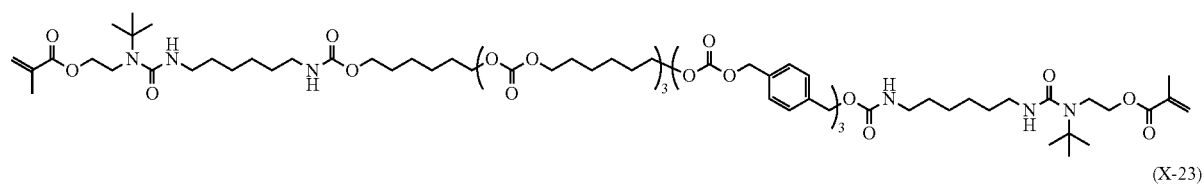

(X-22)

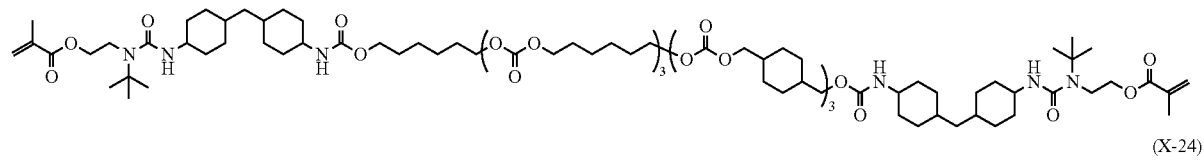

(X-23)

(X-24)

The photo-curable composition may include, as the blocked isocyanate (a1), a single compound or a plurality of compounds. When a plurality of compounds are included as the blocked isocyanate (a1), the mixing ratio of the blocked isocyanate (a1) in the photo-curable composition is calculated on the basis of the total mass of the plurality of compounds.

The mixing ratio of the blocked isocyanate (a1) in the photo-curable composition relative to the total amount (100 mass %) of the photo-curable composition is preferably 10 mass % or more and 90 mass % or less, more preferably 30 mass % or more and 70 mass % or less. When the mixing ratio is less than 10 mass %, the cured product obtained by curing the photo-curable composition has lower toughness. When the mixing ratio is more than 80 mass %, the photo-curable composition has higher viscosity and is less easily handled.

Method of Synthesizing Blocked Isocyanate (a1)

Hereinafter, the method of synthesizing the blocked isocyanate (a1) will be described. The method of synthesizing the blocked isocyanate (a1) includes the following step (I) and step (II).

Step (I): step of causing reaction between polyol and diisocyanate

Step (II): step of causing reaction between blocking agent and diisocyanate having polyol skeleton obtained by step (I)

Hereinafter, these steps will be described.

Step (I): Step of Causing Reaction Between Polyol and Diisocyanate

This step is a step of causing a reaction between a polyol and a diisocyanate. This provides a polyisocyanate having a polyol skeleton.

Non-limiting examples of the polyol used in this step include polyether polyol, polyester polyol, polycarbonate polyol, polyalkylene polyol, and polyacetal. These polyols may be used in combination of two or more thereof.

Non-limiting examples of the diisocyanate used in this step include aliphatic diisocyanates such as trimethylene diisocyanate, 1,2-propylene diisocyanate, butylene diisocyanate, hexamethylene diisocyanate, pentamethylene diisocyanate, and trimethylhexamethylene diisocyanate; alicyclic diisocyanates such as cyclohexane diisocyanate, methylcyclohexane diisocyanate, 3-isocyanatomethyl-3,5,5-trimethylcyclohexyl isocyanate (isophorone diisocyanate), methylenebis(cyclohexyl isocyanate) or dicyclohexylmethane diisocyanate, bis(isocyanatomethyl)cyclohexane, and norbornane diisocyanate; and aromatic diisocyanates such as phenylene diisocyanate, tolylene diisocyanate, 4,4'-diphenyl diisocyanate, 1,5-naphthalene diisocyanate, diphenylmethane diisocyanate, and 4,4'-toluidine diisocyanate.

This step is preferably performed such that the polyol and the diisocyanate react in a solvent. The solvent is not particularly limited as long as the polyol and the diisocyanate dissolve therein. Specific examples include dialkyl ethers such as diethyl ether and dipropyl ether; cyclic ethers such as 1,4-dioxane and tetrahydrofuran; ketones such as acetone, methyl ethyl ketone, diisopropyl ketone, and isobutyl methyl ketone; esters such as methyl acetate, ethyl acetate, and butyl acetate; hydrocarbons such as toluene, xylene, and ethylbenzene; halogen-based solvents such as methylene chloride, chloroform, carbon tetrachloride, tetrachloroethane, trichloroethane, and chlorobenzene; and nitriles such as acetonitrile. These solvents may be used alone or in combination of two or more thereof. The solvent employed is preferably a dehydrated solvent from the viewpoint of suppressing decomposition of isocyanate groups of diisocyanate caused by water.

In the reaction of this step, the ratio of the number of moles of diisocyanate to the number of moles of polyol (number of moles of diisocyanate/number of moles of polyol) is preferably 1 or more and 20 or less, more preferably 3 or more and 10 or less. When the ratio is less than 1, a diisocyanate-polyol polyaddition reaction as a side reaction generates unwanted polyurethane to a higher proportion, which results in a lower yield of the target diisocyanate having a polyol skeleton. When the ratio is more than 20, an excess of unreacted diisocyanate remains after the reaction and this unreacted diisocyanate may be difficult to remove.

This step is preferably performed in an inert atmosphere such as nitrogen, helium, or argon. This step is preferably performed at 0° C. or more and 150° C. or less, more preferably performed at 30° C. or more and 100° C. or less. This step may be performed under reflux. When this step is performed at a reaction temperature higher than 150° C., a side reaction occurs at a higher probability. When this step is performed at a reaction temperature of less than 0° C., the reaction occurs at a lower rate, which may result in an increase in the reaction time or a decrease in the yield.

This step may be performed in the presence of a catalyst. Examples of the catalyst include organotin compounds such as tin octanoate, dibutyltin diacetate, dibutyltin dilaurate, and tin 2-ethylhexanoate; naphthenic acid metal salts such as copper naphthenate, zinc naphthenate, and cobalt naphthenate; and tertiary amines such as triethylamine, benzyldimethylamine, pyridine, N,N-dimethylpiperazine, and triethylenediamine. These catalysts may be used alone or in combination of two or more thereof. The amount of catalyst used relative to the total amount (100 mass %) of polyol is preferably 0.001 mass % or more and 10 mass % or less.

The diisocyanate having a polyol skeleton obtained by this step can be isolated and purified by a commonly used isolation process, for example, an isolation process such as reprecipitation using a poor solvent, concentration, or filtration, or an isolation process of a combination of the foregoing.

Step (II): Step of Causing Reaction Between Blocking Agent and Diisocyanate Having Polyol Skeleton Obtained by Step (I)

This step is a step of causing a reaction between a blocking agent and the polyisocyanate having a polyol skeleton obtained by the step (I). This provides a blocked isocyanate according to this embodiment.

This blocking agent is a compound that reacts with isocyanate groups (—NCO) of diisocyanate to protect active isocyanate groups. The isocyanate groups protected with the blocking agent are referred to as blocked isocyanate groups or isocyanate groups blocked. The blocked isocyanate groups are protected with the blocking agent and hence remain stable in an ordinary state.

Heating the blocked isocyanate compound having blocked isocyanate groups causes the blocking agent to leave (be deblocked) from the blocked isocyanate groups, to provide the original isocyanate groups.

The blocking agent used in this step is not particularly limited as long as it is a (meth)acrylic compound having an amino group, but is preferably a compound selected from tert-butylaminoethyl (meth)acrylate, tert-pentylaminoethyl (meth)acrylate, tert-hexylaminoethyl (meth)acrylate, and tert-butylaminopropyl (meth)acrylate. This enables a decrease in the deblocking temperature of the blocked isocyanate.

This step is preferably performed such that the blocking agent and the diisocyanate having a polyol skeleton react in a solvent. The solvent is not particularly limited as long as the blocking agent and the polyisocyanate having a polyol skeleton dissolve therein. Specific examples of the solvent include those described in the step (I).

This step is preferably performed in an inert atmosphere such as nitrogen, helium, or argon. This step is preferably performed at 0° C. or more and 150° C. or less, more preferably performed at 30° C. or more and 80° C. or less. This step may be performed under reflux. When this step is performed at a reaction temperature of less than 0° C., the reaction is less likely to proceed. When this step is performed at a reaction temperature higher than 150° C., the blocking agent itself may be polymerized through a polymerization reaction of (meth)acryloyl groups. This may result in a decrease in the yield.

This step may be performed in the presence of a catalyst. Specific examples of the catalyst include those described in the step (I).

In this step, in order to suppress polymerization of the (meth)acryloyl group of the blocking agent, a polymerization inhibitor may be used. Specific examples include benzoquinone, hydroquinone, catechol, diphenylbenzoquinone, hydroquinone monomethyl ether, naphthoquinone, t-butylcatechol, t-butylphenol, dimethyl-t-butylphenol, t-butylcresol, dibutylhydroxytoluene, and phenothiazine.

The blocked isocyanate obtained by this step can be isolated and purified by the same process as in the step (I).

Chain Extender (d)

The chain extender (d) is a compound that has at least two active hydrogens that react with isocyanate groups provided by deblocking of blocked isocyanate groups of the blocked isocyanate (a1) or a blocked isocyanate (a3) described later.

Examples of the active hydrogens that react with the isocyanate groups include hydrogen atoms in hydroxyl groups, hydrogen atoms in amino groups, and hydrogen atoms in thiol groups. Thus, the chain extender (d) preferably includes a compound that has, in a single molecule, at least two functional groups of the same species or different species selected from the group consisting of a hydroxyl group, an amino group, and a thiol group. From the viewpoint of reactivity, the chain extender (d) more preferably includes at least one selected from the group consisting of a polyol having at least two hydroxyl groups, a polyamine having at least two amino groups, and a polythiol having at least two thiol groups. In particular, when a chain extender (d) having a hydroxyl group is used, from the viewpoint of reactivity, a reaction accelerator (e) described later is preferably used.

Specific examples of the chain extender (d) include linear diols such as ethylene glycol, 1,3-propanediol, 1,4-butanediol, 1,5-pentanediol, 1,6-hexanediol, 1,8-octanediol, 1,9-nonanediol, and 1,10-decanediol; diols having a branched chain such as 2-methyl-1,3-propanediol, 2,2-dimethyl-1,3-propanediol, 2,2-diethyl-1,3-propanediol, 2-methyl-2-propyl-1,3-propanediol, 2,4-heptanediol, 1,4-dimethylolhexane, 2-ethyl-1,3-hexanediol, 2,2,4-trimethyl-1,3-pentanediol, 2-methyl-1,8-octanediol, 2-butyl-2-ethyl-1,3-propanediol, and dimerdiol; diols having an ether group such as diethylene glycol and propylene glycol; diols having an alicyclic structure such as 1,4-cyclohexanediol, 1,4-cyclohexanedimethanol, and 1,4-dihydroxyethylcyclohexane; diols having an aromatic group such as xylylene glycol, 1,4-dihydroxyethylbenzene, and 4,4'-methylenebis(hydroxyethylbenzene); polyols such as glycerol, trimethylolpropane, and pentaerythritol; hydroxyamines such as N-methylethanolamine and N-ethylethanolamine; polyamines such as ethylenediamine, 1,3-diaminopropane, hexamethylenediamine, triethylenetetramine, diethylenetriamine, isophoronediamine, 4,4'-diaminodicyclohexylmethane, 2-hydroxyethylpropylenediamine, di-2-hydroxyethylethylenediamine, di-2-hydroxyethylpropylenediamine, 2-hydroxypropylethylenediamine, di-2-hydroxypropylethylenediamine, 4,4'-diphenylmethanediamine, methylenebis(o-chloroaniline), xylylenediamine, diphenyldiamine, tolylenediamine, hydrazine, piperazine, and N,N'-diaminopiperazine; aliphatic polythiols such as 1,2-ethanedithiol, 1,2,3-propanetrithiol, 1,2-cyclohexanedithiol, bis(2-mercaptoethyl) ether, tetrakis(mercaptomethyl)methane, diethylene glycol bis(2-mercaptoacetate), trimethylolpropane tris(3-mercaptopropionate), trimethylolpropane tris(2-mercaptoacetate), pentaerythritol tetrakis(2-mercaptoacetate), pentaerythritol tetrakis(3-mercaptopropionate), hydroxymethyl sulfide bis(2-mercaptoacetate), hydroxymethyl sulfide bis(3-mercaptopropionate), 1,1,3,3-tetrakis(mercaptomethylthio)propane, and tris(mercaptoethylthio)methane; aromatic polythiol compounds such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,3,5-trimercaptobenzene, 1,3,5-tris(mercaptomethyl)benzene, 1,3,5-tris(mercaptomethyleneoxy)benzene, 1,3,5-tris(mercaptoethyleneoxy)benzene, 2,5-toluenedithiol, 3,4-toluenedithiol, 1,5-naphthalenedithiol, and 2,6-naphthalenedithiol; and water. These chain extenders may be used alone or in combination of two or more thereof.

Of these, from the viewpoint of providing well-balanced properties of a cured product obtained by photo-curing and subsequently heat-treating the photo-curable composition as described later, and being available industrially and inexpensively in large amounts, preferred are 1,4-butanediol, 1,5-pentanediol, 1,6-hexanediol, 1,8-octanediol, 1,9-nonanediol, 1,10-decanediol, 1,4-cyclohexanedimethanol, 1,4-dihydroxyethylcyclohexane, ethylenediamine, 1,3-diaminopropane, isophoronediamine, and 4,4'-diaminodicyclohexylmethane.

The ratio of the number of moles of the chain extender (d) to the number of moles of the blocked isocyanate (a1) (number of moles of chain extender (d)/number of moles of blocked isocyanate (a1)) is preferably 0.1 or more and 5 or less, more preferably 0.5 or more and 3 or less. As described later, when the photo-curable composition according to this embodiment is photo-cured and subsequently heat-treated, isocyanate groups are restored and the isocyanate groups and the chain extender (d) react to form bonds such as urethane bonds. However, when the ratio is less than 0.1, the isocyanate groups and the chain extender (d) react at lower efficiency, so that the three-dimensional article finally obtained by photo-curing and subsequent heat treatment tends to have less good mechanical characteristics. When the ratio is more than 5, an excess of the chain extender (d) remains unreacted within the three-dimensional article, so that the three-dimensional article finally obtained by photo-curing and subsequent heat treatment tends to have less good mechanical characteristics.

Reaction Accelerator (e)

In this embodiment, as described above, the polyrotaxane having at least one functional group selected from a (meth)acryloyl group and a hydroxyl group is included. The reaction accelerator (e) is a compound that, in the case of using the chain extender (d) that is a compound having a hydroxyl group, or in the case of using the polyrotaxane (c) having a hydroxyl group, accelerates the reaction between the hydroxyl group and an isocyanate group provided by deblocking of the blocked isocyanate group of the blocked isocyanate (a1). Examples of the reaction accelerator include tin compounds such as dibutyltin dilaurate, dioctyltin dilaurate, and dibutyltin dioctanoate.

Such reaction accelerators (e) may be used alone or in combination of two or more thereof. The amount of reaction accelerator (e) used relative to the total amount (100 mass %) of the polyol is preferably 0.001 mass % or more and 10 mass % or less.

Functions of Photo-Curable Composition

The three-dimensional-forming photo-curable composition according to this embodiment includes the polyrotaxane (c) having at least one functional group selected from a (meth)acryloyl group and a hydroxyl group. Thus, as in the first embodiment, when this composition is cured by irradiation with light, it provides a cured product (three-dimensional article) having higher toughness than before.

The three-dimensional-forming photo-curable composition according to this embodiment may be cured (photo-cured) by irradiation with light and subsequently heat-treated to achieve even higher toughness. This reaction scheme will be described with reference to FIG. 2. FIG. 2 is a schematic view illustrating a reaction scheme in which the photo-curable composition according to this embodiment is cured by irradiation with light, and subsequently heat-treated.

When the polyrotaxane having a (meth)acryloyl group is used and the photo-curable composition according to this embodiment is irradiated with light of a predetermined wavelength (such as ultraviolet rays), the photo-radical generator (b) in the photo-curable composition generates a radical. This causes a polymerization reaction of the (meth)acryloyl groups of the blocked isocyanate (a1), resulting in solidification. At this time, another polymerization reaction proceeds between the polyrotaxane (c) having a (meth)acryloyl group and the blocked isocyanate (a1). When the photo-curable composition includes a reactive diluent such as another radical polymerizable compound, a polymerization reaction proceeds in an appropriate combination among three components of the blocked isocyanate (a1), the polyrotaxane (c), and the reactive diluent. Thus, as schematically illustrated in FIG. 2(B), a photo-cured product is generated. As in the first embodiment, this photo-cured product has movable crosslinking points, and hence has higher toughness than in the case where the photo-curable composition does not include the polyrotaxane (c).

Subsequently, the obtained photo-cured product is heat-treated. As a result, as schematically illustrated in FIG. 2(C), leaving of blocking moieties (BL) derived from the blocking agent, namely, deblocking proceeds, so that isocyanate groups (—NCO) are restored. The restored isocyanate groups immediately react with the chain extender (d). Thus, when the chain extender (d) has a hydroxyl group, urethane bonds are formed due to the effect of the reaction accelerator (e); when the chain extender (d) has an amino group, urea bonds are formed. As a result, a cured product schematically illustrated in FIG. 2(D) is obtained.

On the other hand, when the polyrotaxane having a hydroxyl group is used and the photo-curable composition according to this embodiment is irradiated with light of a predetermined wavelength (such as ultraviolet rays), the photo-radical generator (b) in the photo-curable composition generates a radical. This causes a polymerization reaction of the (meth)acryloyl group of the blocked isocyanate (a1), resulting in solidification. When the photo-curable composition further includes a reactive diluent such as another radical polymerizable compound, a polymerization reaction proceeds in an appropriate combination between two components of the blocked isocyanate (a1) and the reactive diluent. As a result, as schematically illustrated in FIG. 3(B), a photo-cured product is generated.

Subsequently, the obtained photo-cured product is heat-treated. Thus, as schematically illustrated in FIG. 3(C), leaving of blocking moieties (BL) derived from the blocking agent, namely, deblocking proceeds, so that isocyanate groups (—NCO) are restored. The restored isocyanate groups immediately react with, due to the effect of the reaction accelerator (e), hydroxyl groups of the polyrotaxane (c), to form urethane bonds. As in the first embodiment, this photo-cured product has movable crosslinking points, and hence has higher toughness than in the case where the photo-curable composition does not include the polyrotaxane (c).

As a result, as schematically illustrated in FIG. 3(D), a cured product is obtained.

As described above, the photo-curable composition according to this embodiment is photo-cured and subsequently heat-treated, to cause deblocking; the deblocking achieves a decrease in the crosslinking density of post-photo-curing. In addition, urethane bonds or urea bonds are formed, to provide a cured product having a polyurethane structure, a polyurea structure, or a mixed structure thereof. This results in even higher toughness.

It is known that the degree of improvement (by adding a toughness improvement component to a curable composition) in the toughness of a cured product obtained by curing the curable composition is affected by the crosslinking density of the cured product. Specifically, on a cured product having a high crosslinking density, the toughness improvement component exerts a weaker toughness improvement effect; conversely, a stronger improvement effect is exerted on a cured product having a lower crosslinking density. In this embodiment, as the polymerizable compound (a), the blocked isocyanate (a1) having a (meth)acryloyl group is used, so that, as described above, performing photo-curing and subsequent heat treatment causes the deblocking reaction, to thereby break bonds in the photo-cured product. In other words, the heat treatment achieves a decrease in the crosslinking density of the cured product. Thus, in this embodiment, the heat treatment is performed to achieve a lower crosslinking density than in existing photo-cured products, so that the polyrotaxane (c) serving as a toughness improvement component exerts a stronger toughness improvement effect.

Photo- and Heat-Cured Product

The cured product (photo- and heat-cured product) obtained by photo-curing and subsequently heat-treating the photo-curable composition according to this embodiment will be described. The photo- and heat-cured product (resin) according to this embodiment includes a repeating structural unit represented by the following general formula (8), a repeating structural unit represented by the following general formula (9), and a polyrotaxane structure.

(8)

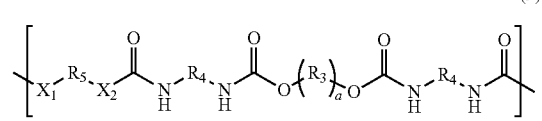

(9)

In the formula (8), $R_1$ represents a hydrogen atom or a methyl group, $R_2$ represents a hydrocarbon group that has 1 to 10 carbon atoms and may have a substituent, and $L_1$ represents a divalent hydrocarbon group that has 1 to 10 carbon atoms and may have a substituent. In the formula (9), $R_3$, $R_4$, and $R_5$ each independently represent a hydrocarbon group that has 1 to 20 carbon atoms and may have a substituent, $X_1$ and $X_2$ each independently represent any one of O (oxygen atom), S (sulfur atom), and NH (imino group), and a is an integer of 1 or more and 100 or less.

In the formula (8) and formula (9), when any one of $L_1$, $R_2$, $R_3$, $R_4$, and $R_5$ has a substituent, the substituent may be a substituent including a carbon atom. However, in this case, the substituent bonds to a non-carbon atom of $L_1$, $R_2$, $R_3$, $R_4$, or $R_5$. In this case, the number of carbon atoms included in the substituent is not included in the number of carbon atoms of the "hydrocarbon group". The substituent may include a hetero atom.

In the formula (8), as described above, from the viewpoint of a decrease in the deblocking temperature, $R_2$ is preferably a group selected from a tert-butyl group, a tert-pentyl group, and a tert-hexyl group. In addition, when $R_2$ is any one of the above-described groups, the photo- and heat-cured product is easily synthesized at low costs.

In the formula (8), $L_1$ is preferably, from the viewpoint of ease of availability and ease of synthesis, an ethylene group or a propylene group.

In the formula (9), $R_3$ preferably has, from the viewpoint of ease of availability and ease of synthesis, at least one divalent linking group selected from the group consisting of the following formulas (A-1) to (A-4).

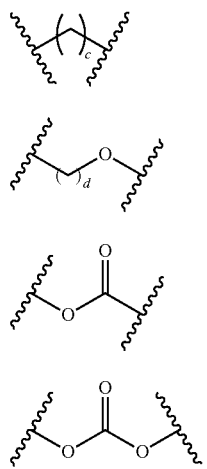

(A-1)

(A-2)

(A-3)

(A-4)

In the formula (A-1), c is an integer of 1 or more and 10 or less. In the formula (A-2), d is an integer of 1 or more and 10 or less.

In the formula (9), $R_3$ preferably has a group represented by the formula (A-4) above. This provides a higher elastic modulus of the photo- and heat-cured product.

The "polyrotaxane structure" is a structure including a plurality of cyclic molecules, a linear molecule penetrating and skewering the plurality of cyclic molecules, and blocking groups disposed at both ends of the linear molecule to prevent the cyclic molecules from leaving. The cyclic molecules, the linear molecule, and the blocking groups are the same as those described above.

In the photo- and heat-cured product according to this embodiment, the repeating structural unit represented by the general formula (8) above bonds to the cyclic molecules in the polyrotaxane structure. The cyclic molecules in the polyrotaxane structure are freely movable along the linear molecule in the polyrotaxane structure. Thus, under the application of an external stress or the like, crosslinking points in the cured product move in accordance with the stress. Thus, in response to the stress, the tension among the polymers becomes uniform. As a result, the photo- and heat-cured product according to this embodiment has high toughness.

Method for Producing Three-Dimensional Article

The photo-curable composition according to this embodiment is suitably applicable to a method for producing a three-dimensional article by an optical three-dimensional-forming method (stereolithography). Hereinafter, the method for producing a three-dimensional article from the photo-curable composition according to this embodiment will be described.

The method for producing a three-dimensional article according to this embodiment includes a step of forming a formed article by stereolithography, and a step of heat-treating the formed article.

Step of Forming Formed Article by Stereolithography

The stereolithography may be performed by a publicly known method. This step includes steps of selectively irradiating a photo-curable composition with an active energy ray on the basis of slice data of a target three-dimensional article, to cure a layer of the photo-curable composition.

In this step, the active energy ray radiated to the photo-curable composition is not particularly limited as long as the active energy ray cures the photo-curable composition according to this embodiment. Specific examples of the active energy ray include electromagnetic waves such as ultraviolet rays, visible light, infrared rays, X-rays, γ-rays, and laser beams; and corpuscular beams such as α-rays, β-rays, and electron beams. Of these, from the viewpoint of the absorption wavelength of the photo-radical generator (c) employed and equipment installation costs, ultraviolet rays are most preferred. The dose is not particularly limited, but is preferably 0.001 J/cm$^2$ or more and 10 J/cm$^2$ or less. When the dose is less than 0.001 J/cm$^2$, the photo-curable composition may not be sufficiently cured. When the dose is more than 10 J/cm$^2$, the irradiation time becomes long, which results in lower productivity.

The method of irradiating the photo-curable composition with an active energy ray is not particularly limited. For example, when light is radiated as the active energy ray, the following methods may be employed. The first method may be a method of using focused point light such as a laser beam, and two-dimensionally scanning this light over the photo-curable composition. In this case, the two-dimensional scanning may be performed by dot-by-dot scanning or line-by-line scanning. The second method may be an area exposure process of radiating light using a projector or the like in accordance with the shape of slice data. In this case, an active energy ray may be radiated to an area through an area scanning mask including a plurality of microoptical shutters arranged, such as liquid crystal shutters or digital micro mirror shutters.

In this step, after a formed article is obtained by stereolithography, the surface of the obtained formed article may be washed with a washing agent such as an organic solvent. The obtained formed article may be subjected to post-curing of radiating light or heat to cure unreacted residual components that may remain in the surface or inside of the formed article. When the post-curing is performed by radiation of heat, it may also serve as the following step of heat-treating the formed article.

Step of Heat-Treating Formed Article

In this embodiment, the formed article obtained by stereolithography is heat-treated to thereby, as described above, cause deblocking to achieve a decrease in the crosslinking density, and to generate polyurethane or polyurea. This provides a three-dimensional article having higher toughness.

The heat treatment temperature in this step is not particularly limited as long as, at the heat treatment temperature, deblocking of blocking moieties proceeds in the formed Blocked Isocyanate (a2)

The blocked isocyanate (a2) is represented by the following general formula (5).

$$A\text{-}D\text{-}C \tag{5}$$

(in the formula (5), A and C each independently represent a group represented by the following formula (2), and D represents a group represented by the following formula (6).

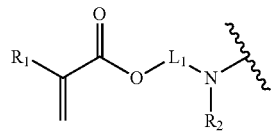

(2)

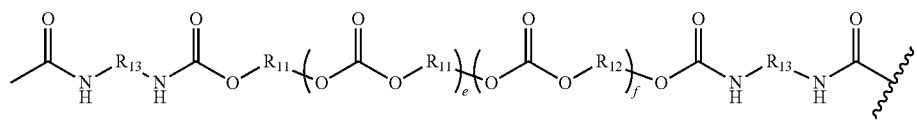

(6)

article, but is preferably 50° C. or more and 200° C. or less, more preferably 100° C. or more and 150° C. or less. When the heat treatment temperature is less than 50° C., deblocking does not proceed, so that the effect of improving toughness may not be sufficiently exerted. When the heat treatment temperature is more than 200° C., the resin may deteriorate, so that the three-dimensional article may become inferior in terms of various mechanical characteristics.

The heat treatment time in this step is not particularly limited as long as, over the heat treatment time, deblocking of the blocking moieties sufficiently proceeds in the formed article, but is preferably 0.5 hours or more and 10 hours or less. When the heat treatment time is less than 0.5 hours, deblocking may not proceed, so that the effect of improving toughness may not be sufficiently exerted. The heat treatment time more than 10 hours is disadvantageous in productivity and degradation of various mechanical characteristics of the three-dimensional article due to deterioration of the resin.

Third Embodiment

The photo-curable composition according to this embodiment includes, as the blocked isocyanate (a1) in the second embodiment, a blocked isocyanate (a2) having a (meth) acryloyl group described later. Specifically, the photo-curable composition according to the third embodiment includes, in the case where the polyrotaxane has a (meth) acryloyl group, a blocked isocyanate (a2), a photo-radical generator (b), a polyrotaxane (c), and a chain extender (d); or the photo-curable composition according to the third embodiment includes, in the case where the polyrotaxane has a hydroxyl group, a blocked isocyanate (a2), a photo-radical generator (b), a polyrotaxane (c), and a reaction accelerator (e).

Hereinafter, components of the photo-curable composition according to this embodiment will be described in detail.

Incidentally, in the following description, the same explanations as in the first embodiment and the second embodiment may be omitted.

In the formula (2), $R_1$ represents a hydrogen atom or a methyl group, $R_2$ represents a hydrocarbon group that has 1 to 10 carbon atoms and may have a substituent, and $L_1$ represents a divalent hydrocarbon group that has 1 to 10 carbon atoms and may have a substituent. In the formula (6), $R_{11}$, $R_{12}$, and $R_{13}$ each independently represent a divalent hydrocarbon group that has 1 to 20 carbon atoms and may have a substituent; and e and f are integers that satisfy $1 \leq e+f \leq 50$, provided that one of e and f may be 0.)

In the formula (2) and the formula (6), when any one of $L_1$, $R_2$, $R_{11}$, $R_{12}$, and $R_{13}$ has a substituent, the substituent may be a substituent including a carbon atom. However, in this case, the substituent bonds to a non-carbon atom of $L_1$, $R_2$, $R_{11}$, $R_{12}$, or $R_{13}$. In this case, the number of carbon atoms of the substituent is not included in the number of carbon atoms of the "hydrocarbon group".

In the formula (2), $R_2$ is preferably a group selected from a tert-butyl group, a tert-pentyl group, and a tert-hexyl group. This is preferable because it provides a decrease in the temperature of deblocking (deblocking temperature) during heat treatment of the photo-cured photo-curable composition. When $R_2$ is any one of the above-described groups, the blocked isocyanate (a2) is easily synthesized. When $R_2$ is any one of the above-described groups, the blocked isocyanate (a2) is synthesized at low costs.

In the formula (2), $L_1$ is preferably, from the viewpoint of ease of availability and ease of synthesis, an ethylene group or a propylene group.

In the formula (6), $R_{11}$ and $R_{12}$ each independently represent preferably any one of the following formulas (B-1) to (B-9). This provides even higher elastic modulus and strength of a cured product obtained by photo-curing and subsequently heat-treating a photo-curable composition as described later.

(B-1)

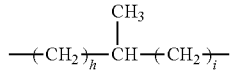

(B-2)

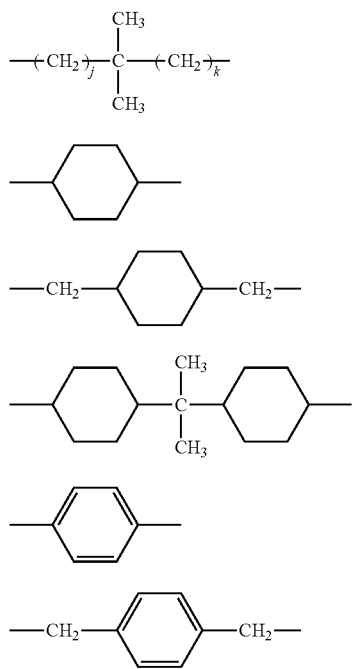

(B-3)
(B-4)
(B-5)
(B-6)
(B-7)
(B-8)

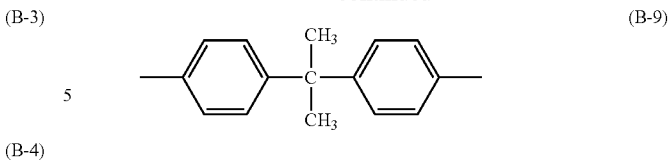

(B-9)

In the formula (B-1), g is an integer of 1 to 10. In the formula (B-2), h and i are integers that satisfy $1 \leq h+i \leq 10$, provided that one of h and i may be 0. In the formula (B-3), j and k are integers that satisfy $1 \leq j+k \leq 10$, provided that one of j and k may be 0.

In the formula (5), A and C are preferably the same. In other words, the blocked isocyanate (a2) is preferably represented by the following general formula (7). In this case, the blocked isocyanate (a2) is synthesized inexpensively and easily.

$$A\text{-}D\text{-}A \tag{7}$$

(in the formula (7), A represents a group represented by the formula (2) above, and D represents a group represented by the formula (6) above.)

Examples of the specific structure of the blocked isocyanate (a2) include the following structures.

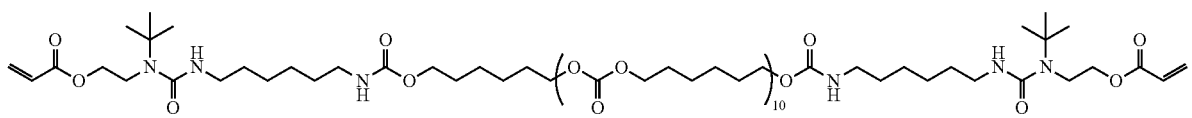

(Y-1)

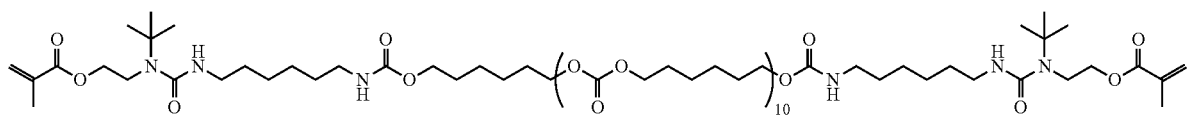

(Y-2)

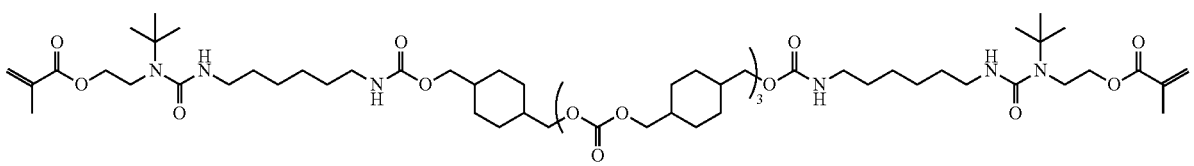

(Y-3)

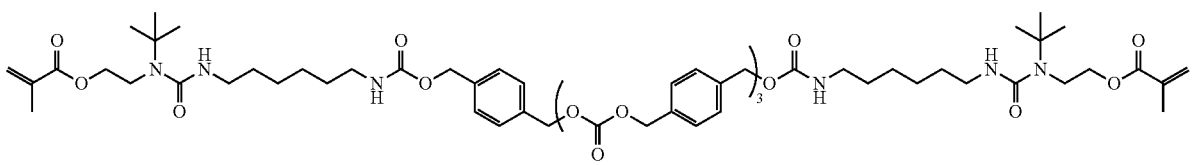

(Y-4)

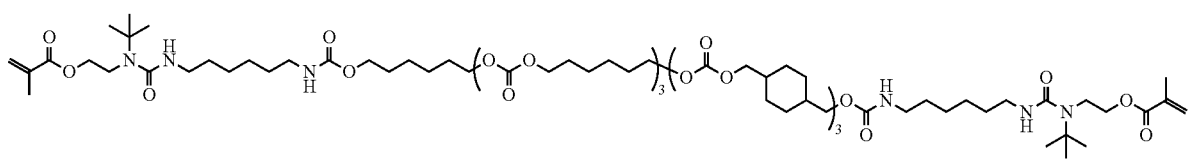

(Y-5)

-continued
(Y-6)
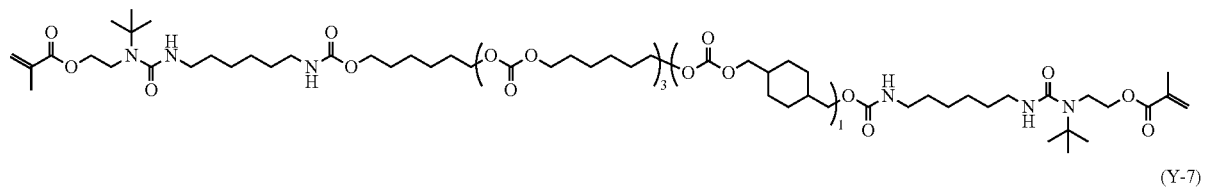
(Y-7)
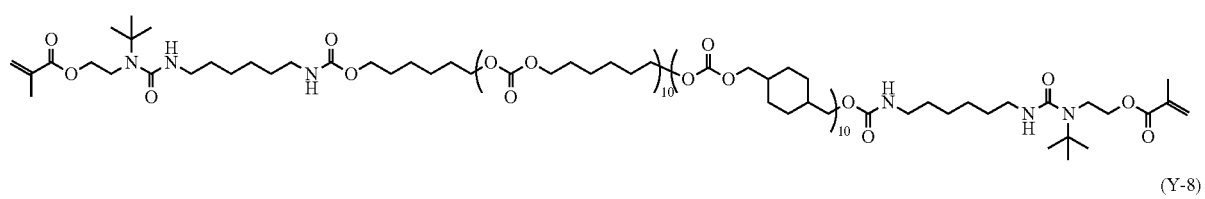
(Y-8)
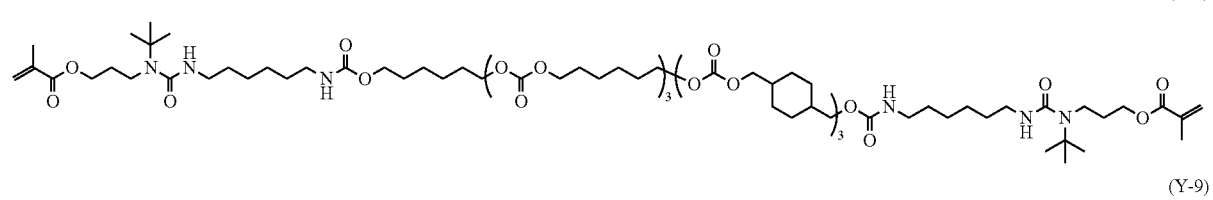
(Y-9)
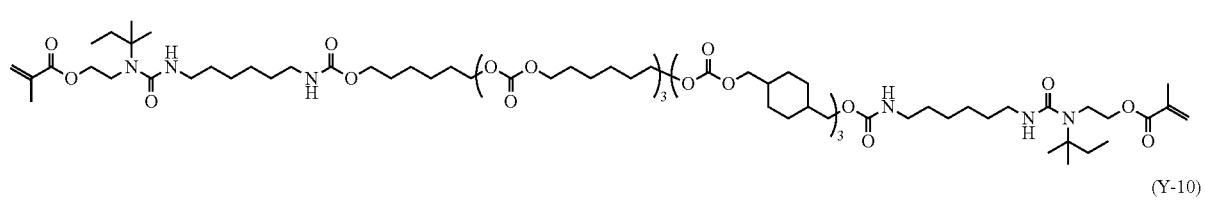
(Y-10)
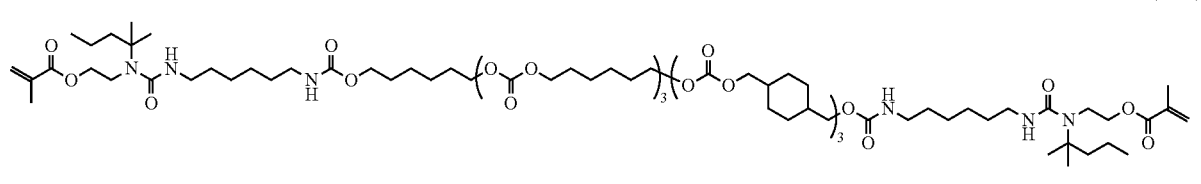
(Y-11)
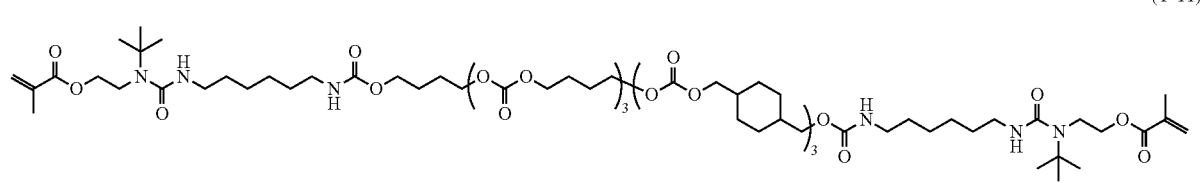
(Y-12)
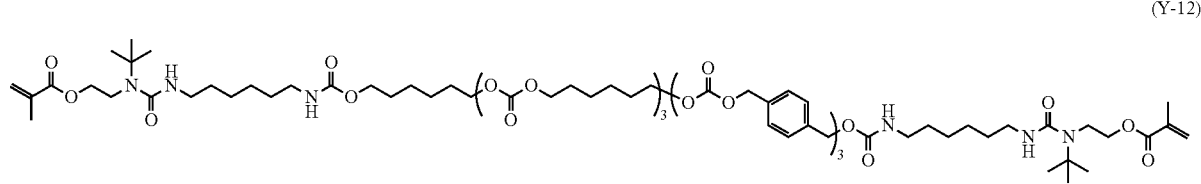
(Y-13)
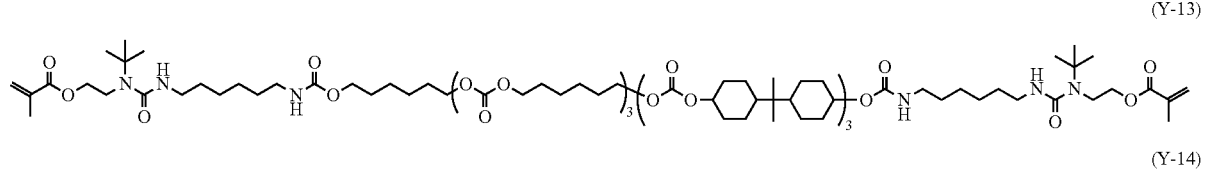
(Y-14)
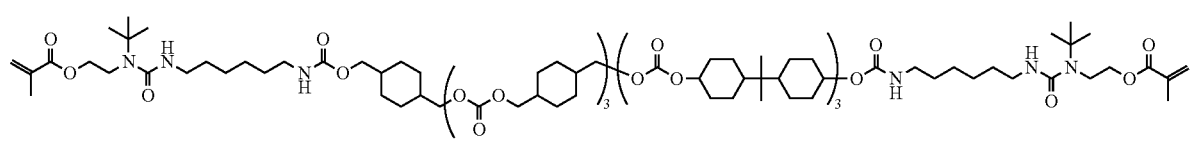

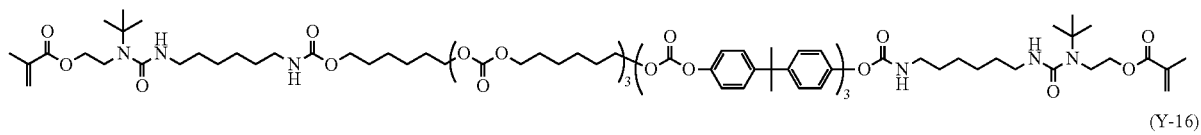
(Y-15)

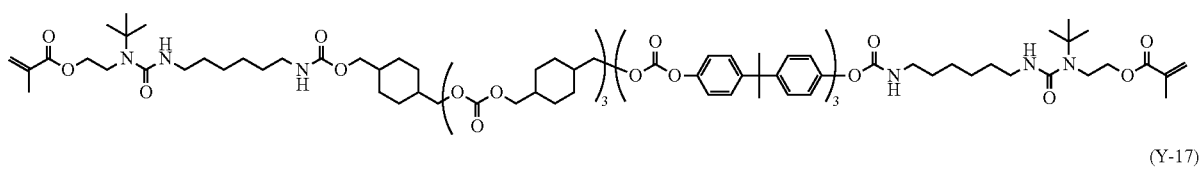
(Y-16)

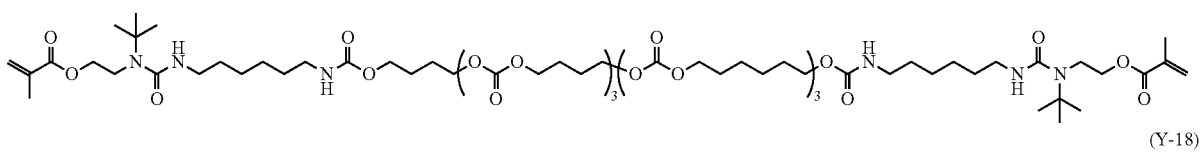
(Y-17)

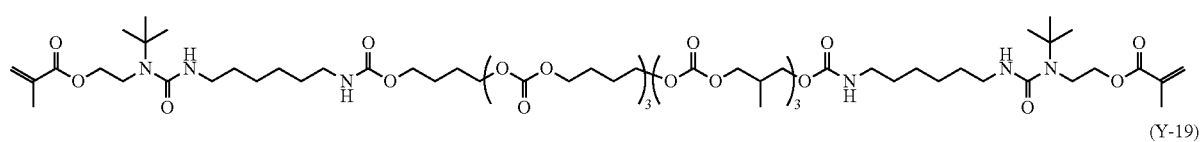
(Y-18)

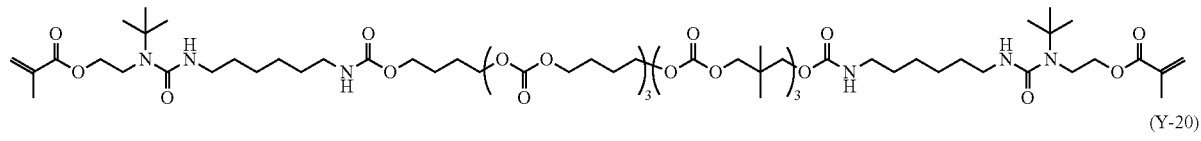
(Y-19)

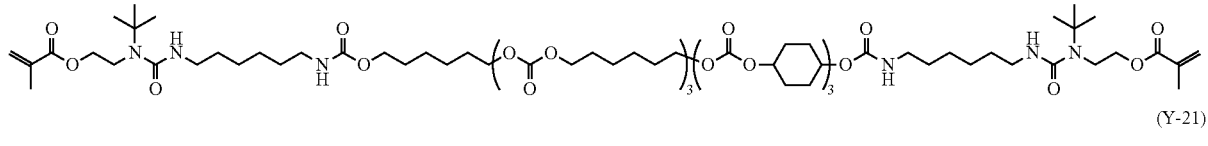
(Y-20)

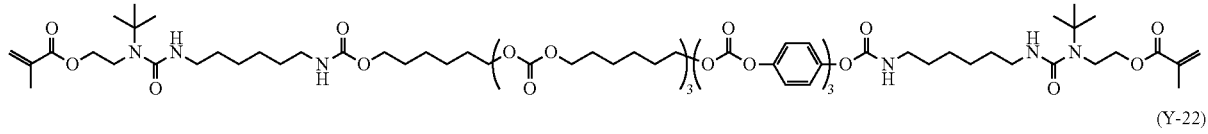
(Y-21)

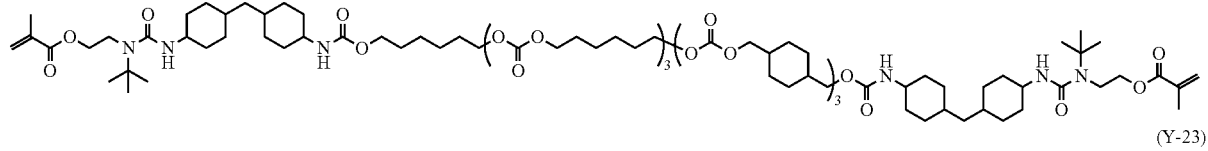
(Y-22)

(Y-23)

Method of Synthesizing Blocked Isocyanate (a2)

Hereinafter, a method of synthesizing the blocked isocyanate (a2) will be described. The method of synthesizing the blocked isocyanate (a2) includes the following step (I)' and step (II).

Step (I)': step of causing reaction between polycarbonatediol and diisocyanate

Step (II): step of causing reaction between blocking agent and diisocyanate having polycarbonate skeleton and obtained by step (I)'

The step (I)' is the same as the step (I) in the second embodiment except that the polyol is replaced by polycarbonatediol. The same explanations as in the second embodiment will be omitted.

The polycarbonatediol used in this step is synthesized by, for example, transesterification between a carbonate compound and a diol.

Non-limiting examples of the carbonate compound used for synthesizing the polycarbonatediol include dialkyl carbonates such as dimethyl carbonate and diethyl carbonate; alkylene carbonates such as ethylene carbonate and propylene carbonate; and diaryl carbonates such as diphenyl carbonate, dinaphthyl carbonate, dianthryl carbonate, diphenanthryl carbonate, diindanyl carbonate, and tetrahydronaphthyl carbonate. These carbonate compounds may be used in combination of two or more thereof.

Non-limiting examples of the diol used for synthesizing the polycarbonatediol include aliphatic diols such as ethylene glycol, diethylene glycol, propylene glycol, 1,4-butanediol, 1,3-butanediol, 1,5-pentanediol, neopentyl glycol, 3-methyl-1,5-pentanediol, 1,6-hexanediol, 1,4-cyclohexanedimethanol, 2-methyl-1,8-octanediol, and 1,9-nonanediol; alicyclic diols such as cyclohexanediol, hydrogenated bisphenol-A, hydrogenated bisphenol-F, and hydrogenated xylylene glycol; and aromatic diols such as bisphenol-A, bisphenol-F, 4,4'-biphenol, and xylylene glycol. These diols may be used in combination of two or more thereof.

The polycarbonatediol preferably has a number-average molecular weight $M_n$ of 100 or more and 5000 or less. When the polycarbonatediol has a number-average molecular weight $M_n$ of less than 100, the blocked isocyanate finally obtained has a low molecular weight, so that the three-dimensional article obtained by curing the photo-curable composition may have a lower elastic modulus or lower strength. When the polycarbonatediol has a number-average molecular weight $M_n$ of more than 5000, the blocked isocyanate finally obtained may have a high molecular weight, so that the photo-curable composition may have a higher viscosity, which may result in inferior usability.

Non-limiting examples of commercially available products of the polycarbonatediol include ETERNACOLL (registered trademark) UM-90 (3/1) ($M_n$=900), ETERNACOLL UM-90 (1/1) ($M_n$=900), ETERNACOLL UM-90 (⅓) ($M_n$=900), ETERNACOLL UC-100 ($M_n$=1000), ETERNACOLL UH-200 ($M_n$=2000), ETERNACOLL UH-100 ($M_n$=1000), ETERNACOLL PH-200 ($M_n$=2000), and ETERNACOLL PH-100 ($M_n$=1000) (all manufactured by Ube Industries, Ltd.).

Chain Extender (d)

As in the photo-curable composition according to the second embodiment, the photo-curable composition according to this embodiment includes, in the case where the polyrotaxane (c) has a (meth)acryloyl group, a chain extender (d). Explanations of the chain extender (d) according to this embodiment are omitted because they are the same as the descriptions of the chain extender (d) according to the second embodiment except that the blocked isocyanate (a1) is replaced by the blocked isocyanate (a2).

Reaction Accelerator (e)

As with the reaction accelerator according to the second embodiment, the reaction accelerator according to this embodiment is optionally added. Specifically, the reaction accelerator is included in the case where the chain extender (d) has a hydroxyl group and in the case where the polyrotaxane (c) has a hydroxyl group. Explanations of the reaction accelerator (e) according to this embodiment will be omitted because they are the same as the descriptions of the chain extender (d) according to the second embodiment except that the blocked isocyanate (a1) is replaced by the blocked isocyanate (23).

Photo- and Heat-Cured Product

The cured product (photo- and heat-cured product) obtained by photo-curing and sufficiently heat-treating the photo-curable composition according to this embodiment will be described. The photo- and heat-cured product (resin) according to this embodiment includes a repeating structural unit represented by the following general formula (8), a repeating structural unit represented by the following general formula (10), and a polyrotaxane structure.

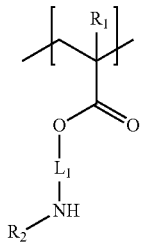

(8)

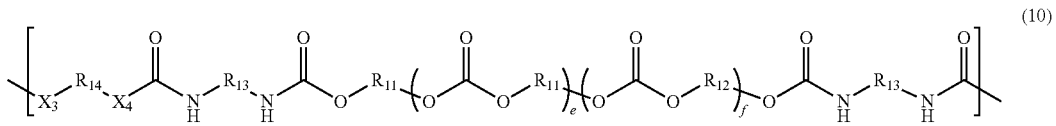

(10)

In the formula (8), $R_1$ represents a hydrogen atom or a methyl group, $R_2$ represents a hydrocarbon group that has 1 to 10 carbon atoms and may have a substituent, and $L_1$ represents a divalent hydrocarbon group that has 1 to 10 carbon atoms and may have a substituent. In the formula (10), $R_{11}$, $R_{12}$, $R_{13}$, and $R_{14}$ each independently represent a divalent hydrocarbon group that has 1 to 20 carbon atoms and may have a substituent, $X_3$ and $X_4$ each independently represent any one of O (oxygen atom), S (sulfur atom), and NH (imino group), and e and f are integers that satisfy 1≤e+f≤50, provided that one of e and f may be 0.

In the formula (8) and formula (10), when any one of $L_1$, $R_2$, $R_{11}$, $R_{12}$, $R_{13}$, and $R_{14}$ has a substituent, the substituent may be a substituent including a carbon atom. However, in this case, the substituent bonds to a non-carbon atom of $L_1$, $R_2$, $R_{11}$, $R_{12}$, $R_{13}$, or $R_{14}$. In this case, the number of carbon atoms of the substituent is not included in the number of carbon atoms of the "hydrocarbon group".

In the formula (8), $R_2$ is preferably, from the viewpoint of a decrease in the deblocking temperature as described above, a group selected from a tert-butyl group, a tert-pentyl group, and a tert-hexyl group. When $R_2$ is any one of the above-described groups, the photo- and heat-cured product is synthesized easily at low costs.

In the formula (8), $L_1$ is preferably, from the viewpoint of ease of availability and ease of synthesis, an ethylene group or a propylene group.

In the formula (10), $R_{11}$ and $R_{12}$ each independently represent preferably any one of the following formulas (B-1) to (B-9). This provides even higher elastic modulus and strength of the photo- and heat-cured product.

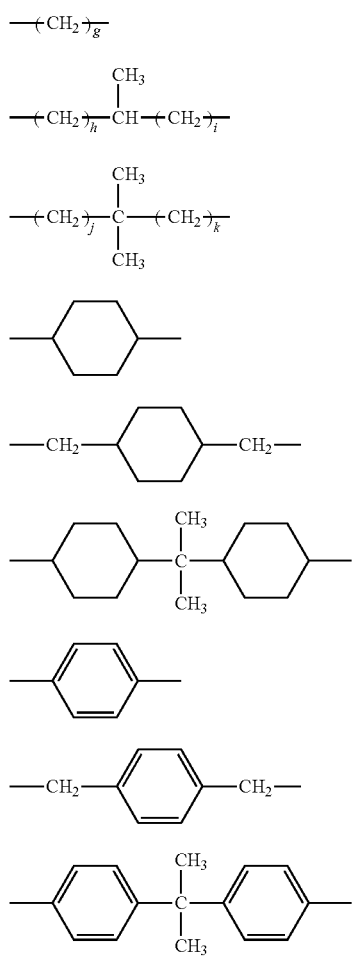

In the formula (B-1), g is an integer of 1 to 10. In the formula (B-2), h and i are integers that satisfy $1 \le h+i \le 10$, provided that one of h and i may be 0. In the formula (B-3), j and k are integers that satisfy $1 \le j+k \le 10$, provided that one of j and k may be 0.

The "polyrotaxane structure" is a structure having a plurality of cyclic molecules, a linear molecule penetrating and skewering the plurality of cyclic molecules, and blocking groups disposed at both ends of the linear molecule to prevent the cyclic molecules from leaving. The cyclic molecules, the linear molecule, and the blocking groups are the same as those described above.

In the photo- and heat-cured product according to this embodiment, in the case of a polyrotaxane having a (meth)acryloyl group, the repeating structural unit represented by the general formula (8) bonds to the cyclic molecules in the polyrotaxane structure. The cyclic molecules in the polyrotaxane structure are freely movable along the linear molecule in the polyrotaxane structure. Thus, under application of an external stress or the like, crosslinking points in the cured product move in accordance with the stress. Thus, in response to the stress, tension among the polymers becomes uniform. As a result, the photo- and heat-cured product according to this embodiment has high toughness.

When the cyclic molecules in the polyrotaxane (c) according to this embodiment have a hydroxyl group and the photo-curable composition according to this embodiment is irradiated with light, a polymerization reaction within the (meth)acrylic compound (a) proceeds. The resultant formed article is heat-treated to obtain a cured product as a result of reactions between a hydroxyl group in the polyrotaxane (c) and an isocyanate group provided by deblocking of a blocked isocyanate group of the blocked isocyanate (a2) described later. The effect of the polyrotaxane provides a cured product having high toughness, compared with existing photo-curable compositions.

Fourth Embodiment

The photo-curable composition according to this embodiment includes, as the polymerizable compound (a) in the first embodiment, a blocked isocyanate (a3) having a branched chain structure. Specifically, the photo-curable composition according to this embodiment includes the blocked isocyanate (a3) having a branched chain structure, the photo-radical generator (b), the polyrotaxane (c), and the chain extender (d).

The blocked isocyanate having a branched chain structure is a (meth)acrylic compound having at least three (meth)acryloyl groups. Examples of the specific structure of the blocked isocyanate having a branched chain structure include a blocked isocyanate represented by the following general formula (11).

(11)

In the formula (11), $A_1$ to $A_4$ are each independently a structure represented by the following general formula (12), and B is a structure represented by the following general formula (13).

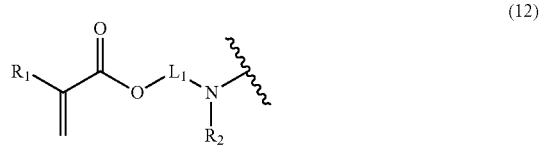

(12)

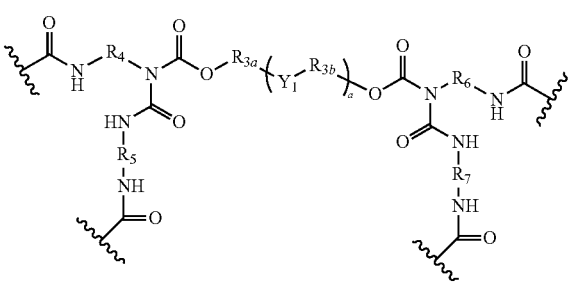

(13)

In the general formula (12), $R_1$ represents a hydrogen atom or a methyl group, $R_2$ represents a hydrocarbon group that has 1 to 10 carbon atoms and may have a substituent, and $L_1$ represents a divalent hydrocarbon group that has 1 to 10 carbon atoms and may have a substituent. In the general formula (13), $R_{3a}$, $R_{3b}$, $R_4$, $R_5$, $R_6$, and $R_7$ each independently represent a divalent hydrocarbon group that has 1 to 20 carbon atoms and may have a substituent, $Y_1$ represents a divalent linking group, and a is an integer of 1 or more and 99 or less. $R_4$ above is the same as $R_4$ in the formula (3).

In the general formula (12) and general formula (13), when any one of $L_1$, $R_2$, $R_{3a}$, $R_{3b}$, $R_4$, $R_5$, $R_6$, and $R_7$ has a substituent, the substituent may be a substituent including a carbon atom. However, in this case, the substituent bonds to a non-carbon atom of $L_1$, $R_2$, $R_{3a}$, $R_{3b}$, $R_4$, $R_5$, $R_6$, or $R_7$. In this case, the number of carbon atoms of the substituent is not included in the number of carbon atoms of the "hydrocarbon group". $R_4$ above is the same as $R_4$ in the formula (3).

In the general formula (12), $R_2$ preferably represents a group selected from a tert-butyl group, a tert-pentyl group, and a tert-hexyl group. This is preferable because it provides a decrease in the temperature of deblocking (deblocking temperature) during heat treatment of the photo-cured photo-curable composition. When $R_2$ is any one of the above-described groups, the blocked isocyanate is easily synthesized. When $R_2$ is any one of the above-described groups, the blocked isocyanate is synthesized at low costs.

In the general formula (12), $L_1$ preferably represents, from the viewpoint of ease of availability and ease of synthesis, an ethylene group or a propylene group.

In the general formula (13), $Y_1$ preferably represents, from the viewpoint of ease of availability and ease of synthesis, at least one divalent linking group selected from the group consisting of the following formulas (C1) to (C3).

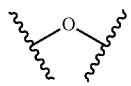
(C1)

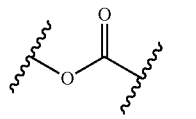
(C2)

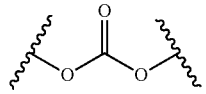
(C3)

In the general formula (11), $A_1$ to $A_4$ are preferably the same. In other words, the blocked isocyanate is preferably represented by the following general formula (14). In this case, the blocked isocyanate is synthesized inexpensively and easily.

(14)

In the general formula (14), A represents a group represented by the general formula (12) above, and B represents a group represented by the general formula (13) above.

The mixing ratio of the blocked isocyanate (a3) having a branched chain structure in the photo-curable composition relative to the total amount (100%) of the photo-curable composition is preferably 0 parts by mass or more and 90 mass % or less, more preferably 0 parts by mass (%) or more and 70 mass % or less. When the mixing ratio is more than 80%, the photo-curable composition has high viscosity and is less easily handled.

Examples of the specific structure of the blocked isocyanate include blocked isocyanates represented by the following formula (I-1) to formula (I-20).

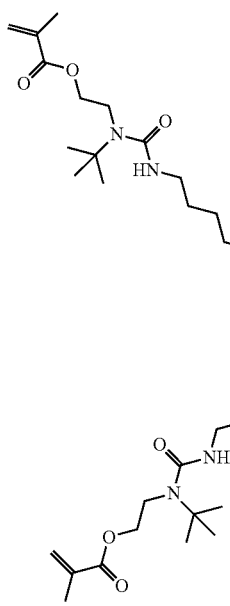
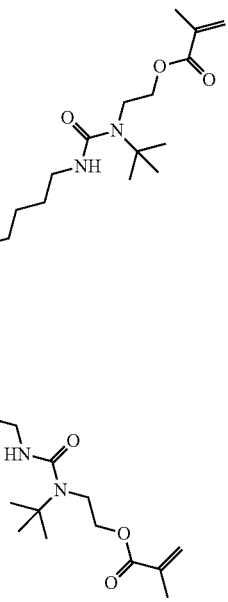
(I-1)

-continued
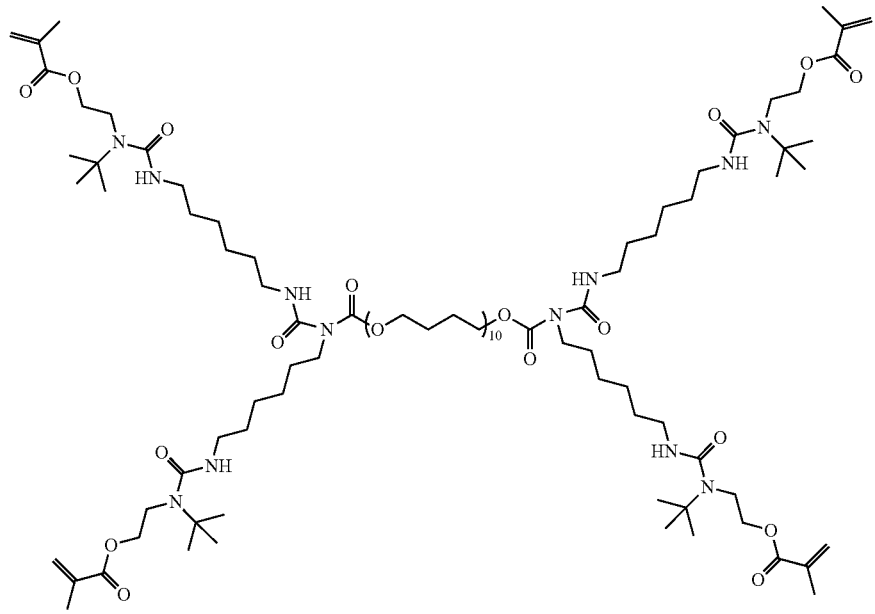
(I-2)
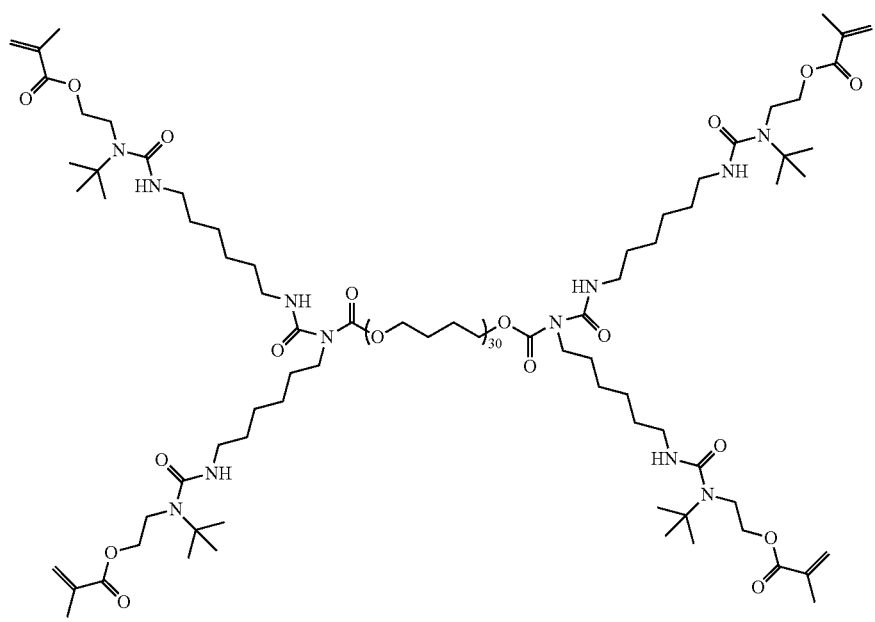
(I-3)

-continued
(I-4)
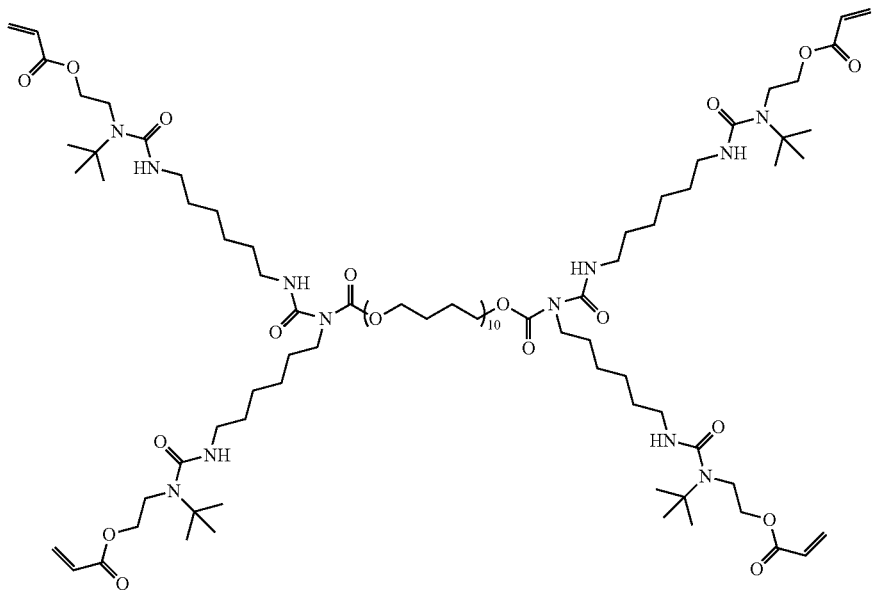
(I-5)
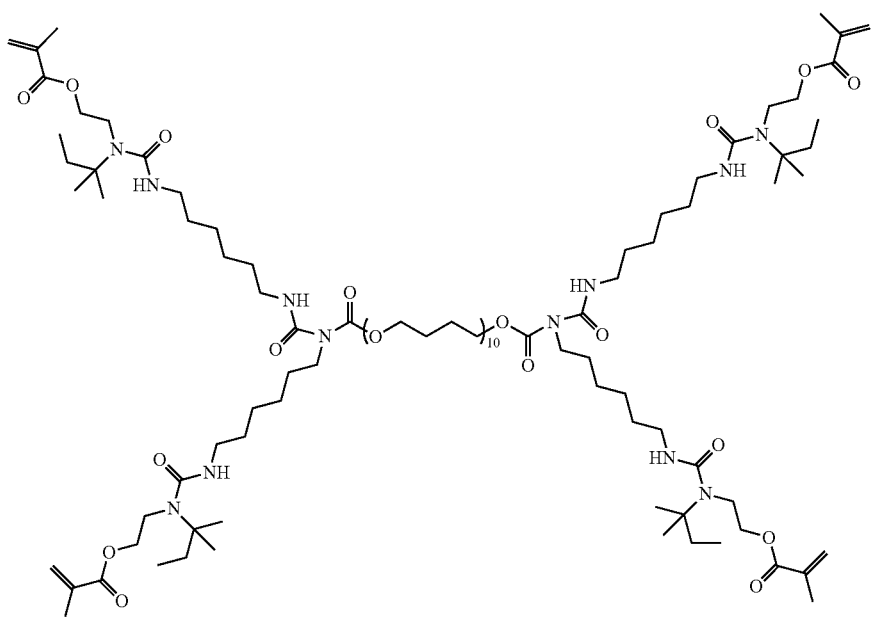

(I-6)
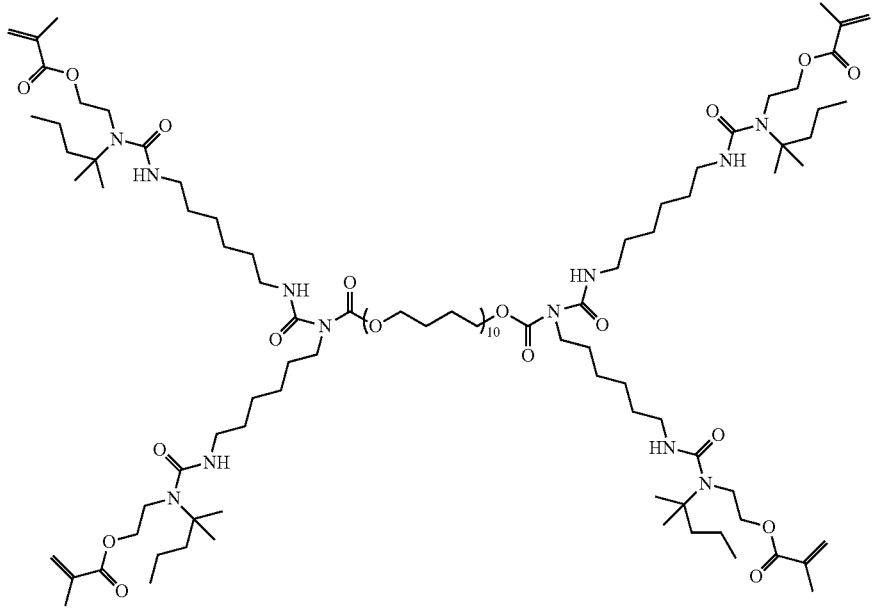
(I-7)
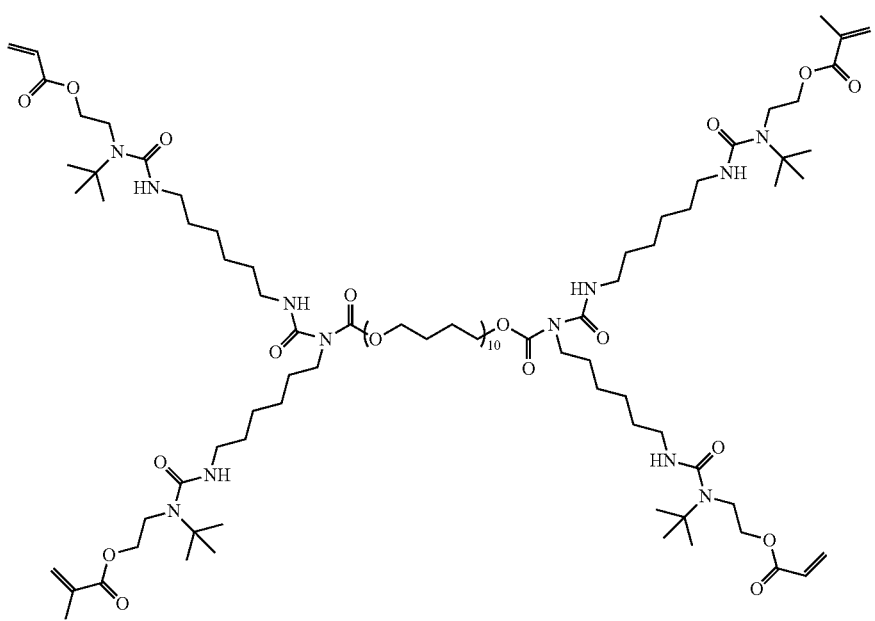

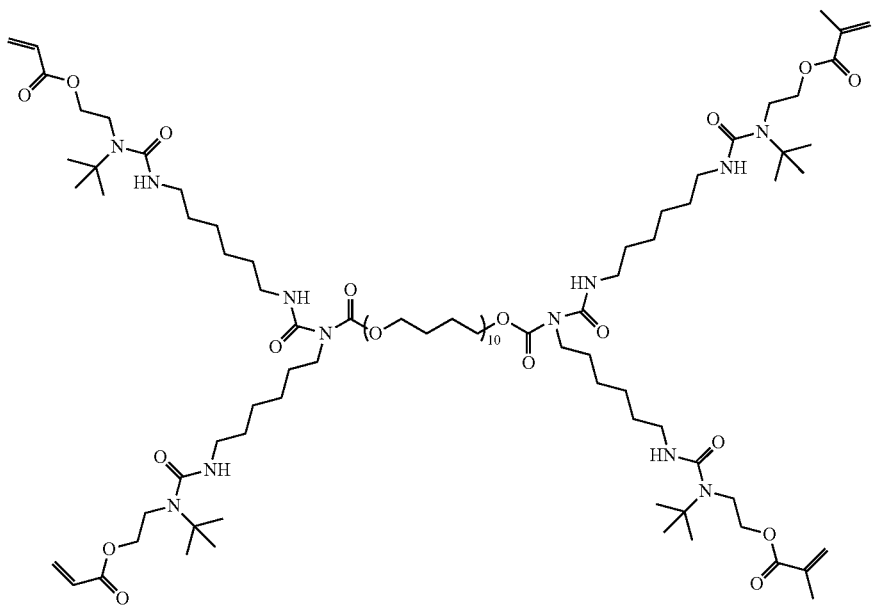
(I-8)
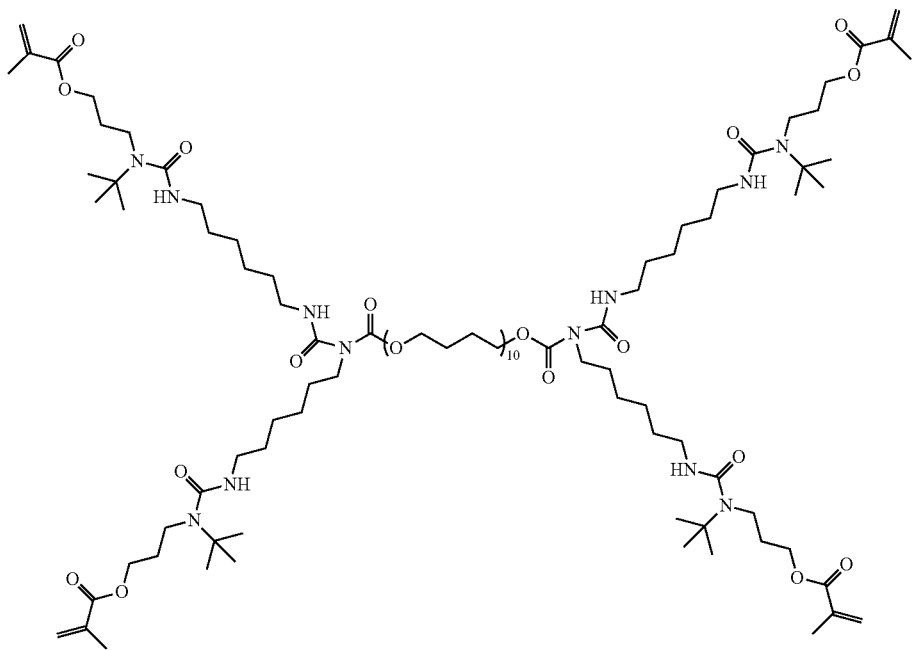
(I-9)

(I-10)
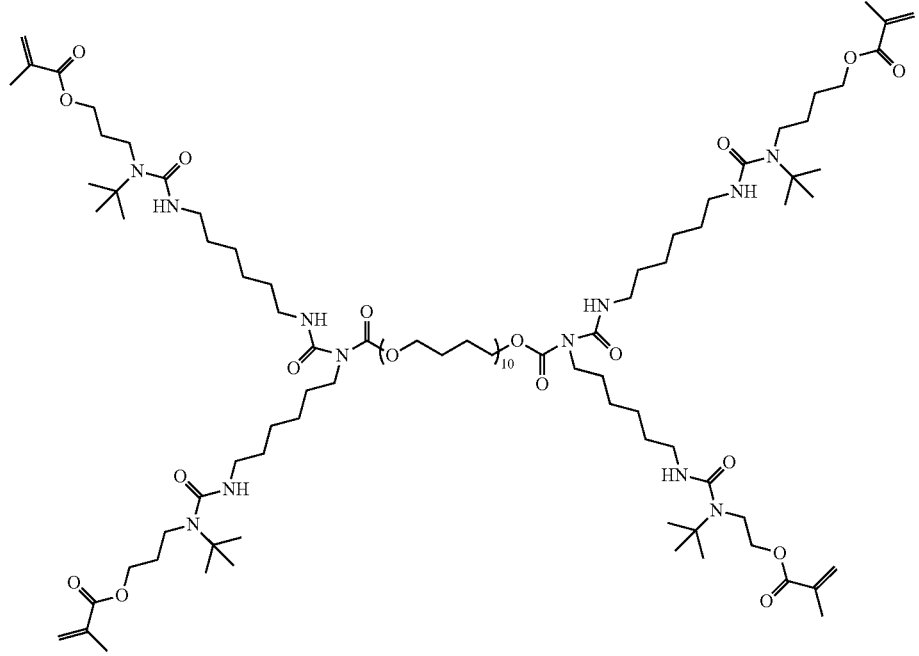
(I-11)
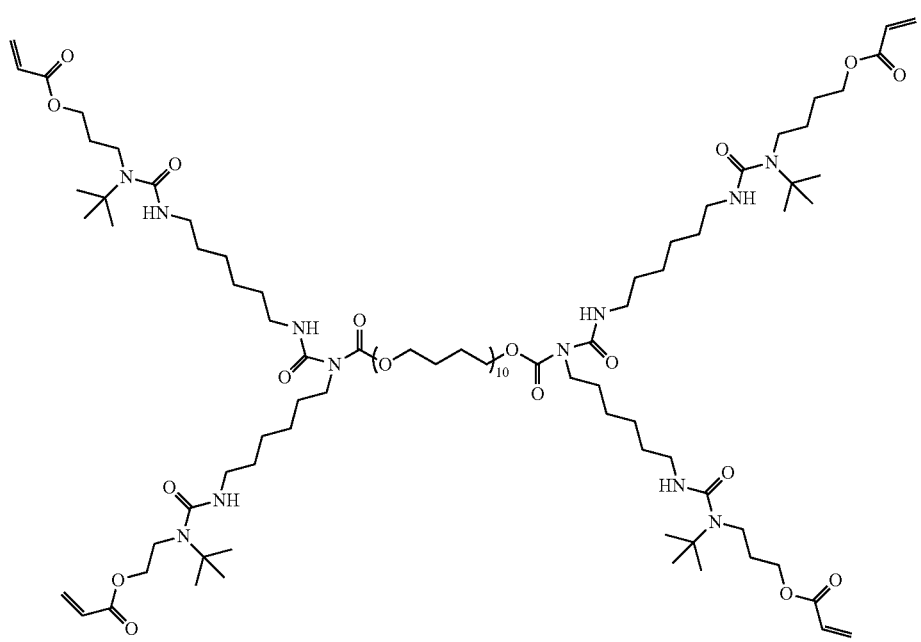

-continued
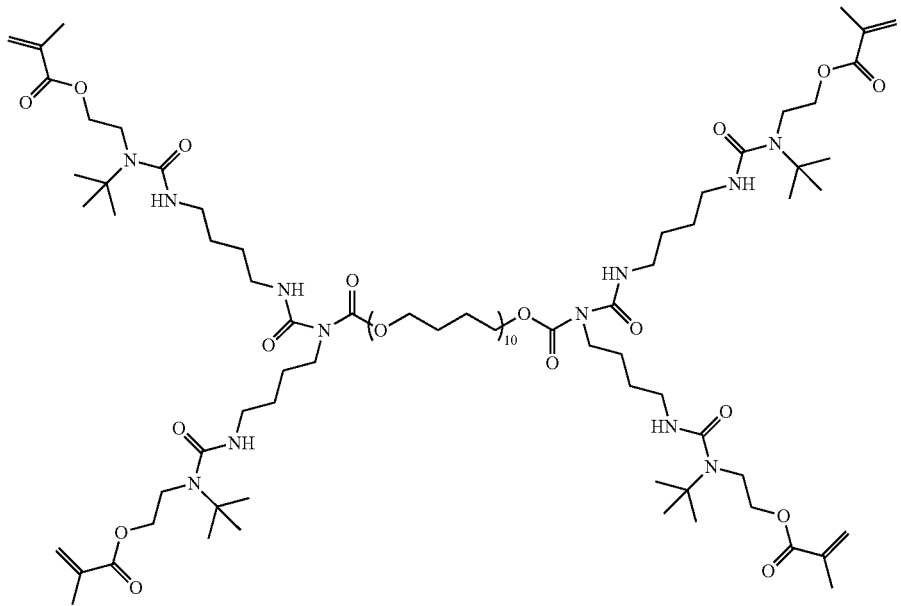
(I-12)
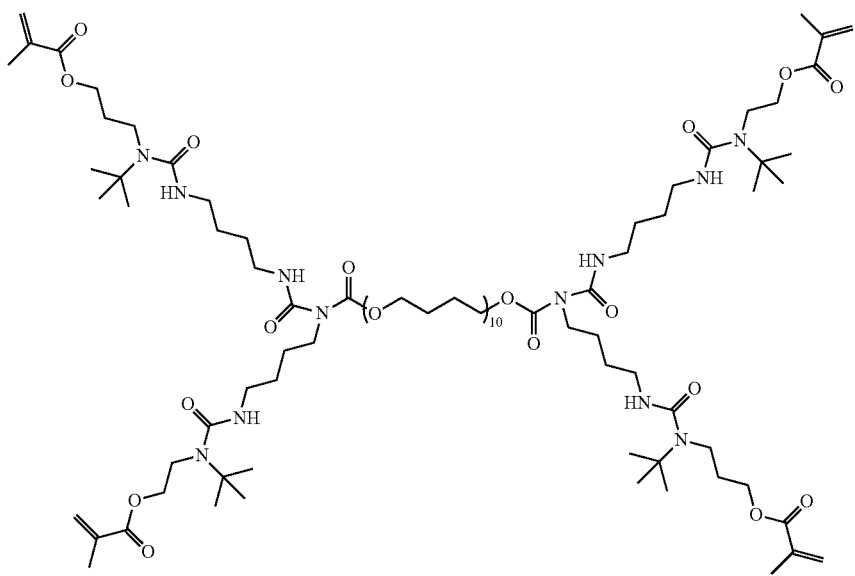
(I-13)

(I-14)
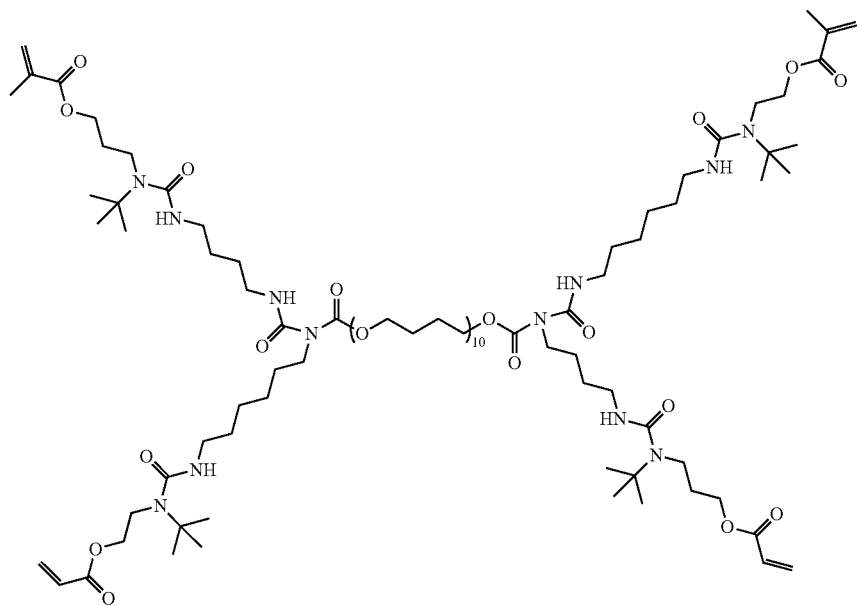
(I-15)
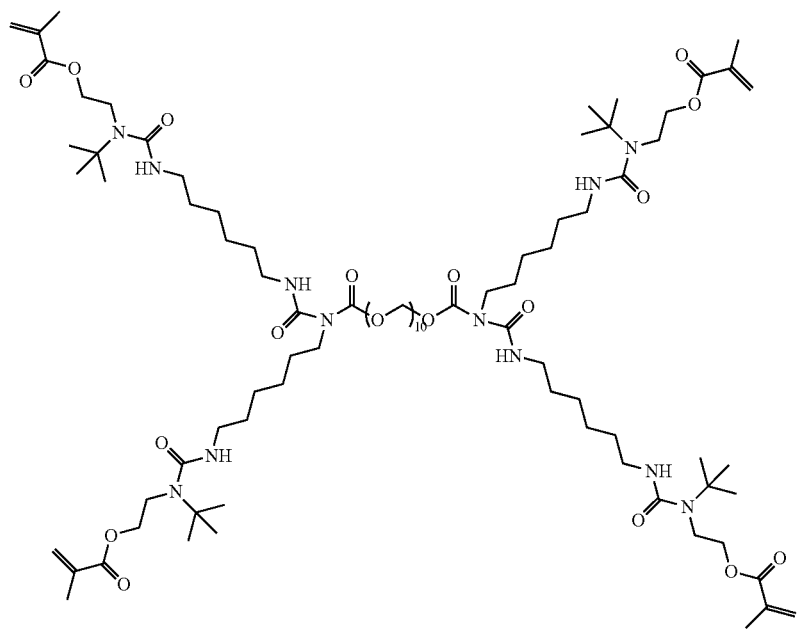

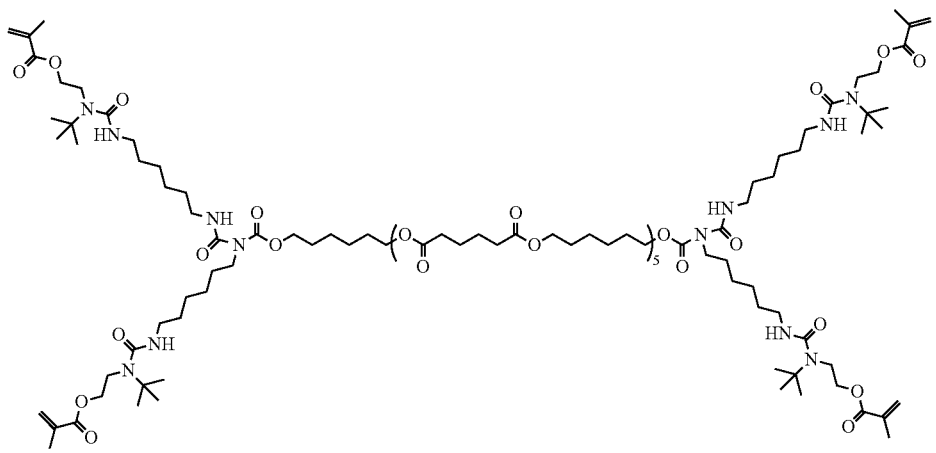
(I-16)
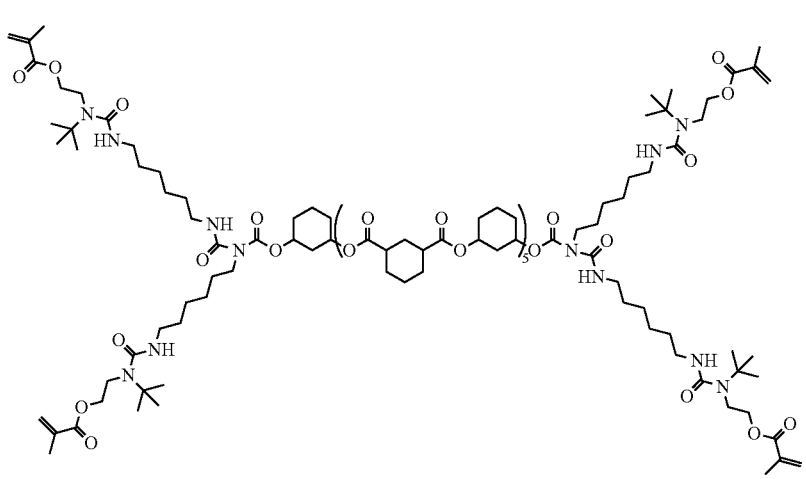
(I-17)
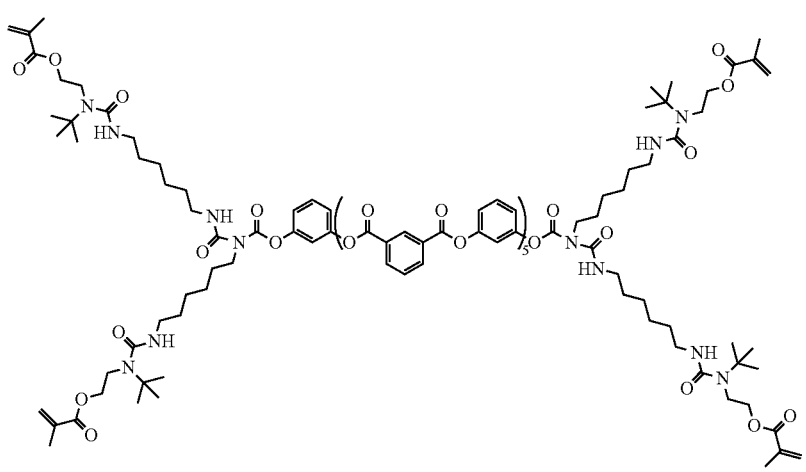
(I-18)

(I-19)

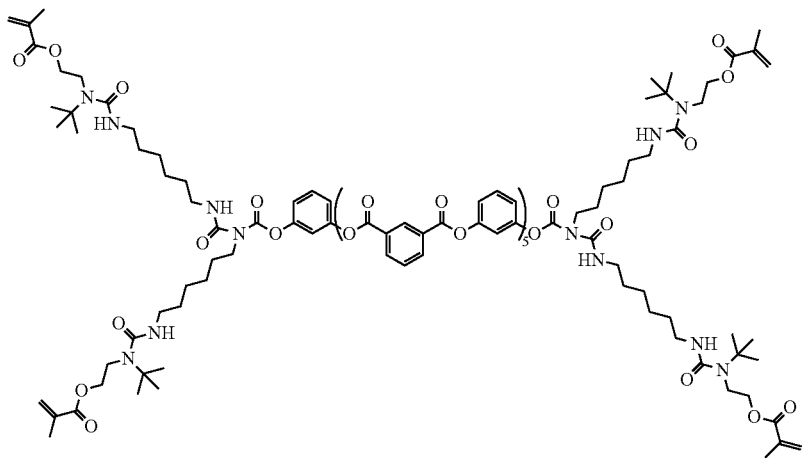

(I-20)

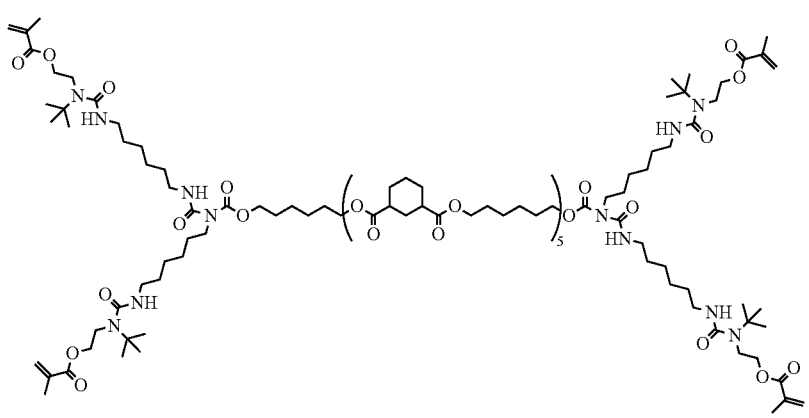

(I-21)

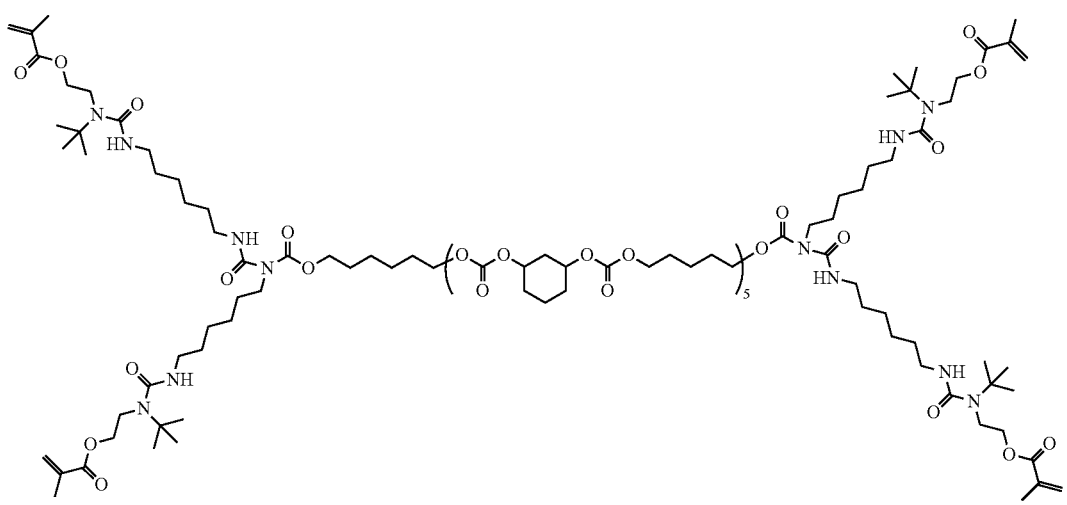

Method of Synthesizing Blocked Isocyanate (a3)

Hereinafter, the method of synthesizing the blocked isocyanate (a3) having a branched chain structure will be described. The method of synthesizing the blocked isocyanate (a3) includes the following step (I) and step (II).

Step (I): step of causing reaction between polyol and diisocyanate

Step (II): step of causing reaction between blocking agent and polyisocyanate having polyol skeleton obtained by step (I)

Hereinafter, these steps will be described.

Step (I): Step of Causing Reaction Between Polyol and Diisocyanate

This step is a step of causing a reaction between a polyol and a diisocyanate. This provides a polyisocyanate having a polyol skeleton.

Non-limiting examples of the polyol used in this step include polyether polyol, polyester polyol, polycarbonate polyol, polyalkylene polyol, and polyacetal. These polyols may be used in combination of two or more thereof.

Non-limiting examples of the diisocyanate used in this step include aliphatic diisocyanates such as trimethylene diisocyanate, 1,2-propylene diisocyanate, butylene diisocyanate, hexamethylene diisocyanate, pentamethylene diisocyanate, and trimethylhexamethylene diisocyanate; alicyclic diisocyanates such as cyclohexane diisocyanate, methylcyclohexane diisocyanate, 3-isocyanatomethyl-3,5,5-trimethylcyclohexyl isocyanate (isophorone diisocyanate), methylenebis(cyclohexyl isocyanate) or dicyclohexylmethane diisocyanate, bis(isocyanatomethyl)cyclohexane, and norbornane diisocyanate; and aromatic diisocyanates such as phenylene diisocyanate, tolylene diisocyanate, 4,4'-diphenyl diisocyanate, 1,5-naphthalene diisocyanate, diphenylmethane diisocyanate, and 4,4'-toluidine diisocyanate.

This step is preferably performed such that the polyol and the diisocyanate react in a solvent. The solvent is not particularly limited as long as the polyol and the diisocyanate dissolve therein. Specific examples include dialkyl ethers such as diethyl ether and dipropyl ether; cyclic ethers such as 1,4-dioxane and tetrahydrofuran; ketones such as acetone, methyl ethyl ketone, diisopropyl ketone, and isobutyl methyl ketone; esters such as methyl acetate, ethyl acetate, and butyl acetate; hydrocarbons such as toluene, xylene, and ethylbenzene; halogen-based solvents such as methylene chloride, chloroform, carbon tetrachloride, tetrachloroethane, trichloroethane, and chlorobenzene; and nitriles such as acetonitrile. These solvents may be used alone or in combination of two or more thereof. The solvent employed is preferably a dehydrated solvent from the viewpoint of suppressing decomposition of isocyanate groups of the diisocyanate compound caused by water.

In the reaction of this step, the ratio of the number of moles of diisocyanate to the number of moles of polyol (number of moles of diisocyanate/number of moles of polyol) is preferably 1 or more and 20 or less, more preferably 3 or more and 10 or less. When the ratio is less than 1, a diisocyanate-polyol polyaddition reaction as a side reaction generates unwanted polyurethane to a higher proportion, which results in a lower yield of the target polyisocyanate having a polyol skeleton. When the ratio is more than 20, an excess of unreacted diisocyanate remains after the reaction and this unreacted diisocyanate may be difficult to remove.

This step is preferably performed in an inert atmosphere such as nitrogen, helium, or argon. This step is preferably performed at 0° C. or more and 150° C. or less, more preferably performed at 30° C. or more and 100° C. or less. This step may be performed under reflux. When this step is performed at a reaction temperature higher than 150° C., a side reaction occurs at a higher probability. When this step is performed at a reaction temperature of less than 0° C., the reaction occurs at a lower rate, which may result in an increase in the reaction time or a decrease in the yield.

This step may be performed in the presence of a catalyst. Examples of the catalyst include organotin compounds such as tin octanoate, dibutyltin diacetate, dibutyltin dilaurate, and tin 2-ethylhexanoate; naphthenic acid metal salts such as copper naphthenate, zinc naphthenate, and cobalt naphthenate; and tertiary amines such as triethylamine, benzyldimethylamine, pyridine, N,N-dimethylpiperazine, and triethylenediamine. These catalysts may be used alone or in combination of two or more thereof. The amount of catalyst used relative to the total amount (100 mass %) of polyol may be 0.001 mass % or more and 1 mass % or less.

The diisocyanate having a polyol skeleton obtained by this step can be isolated and purified by a commonly used isolation process, for example, an isolation process such as reprecipitation using a poor solvent, concentration, or filtration, or an isolation process of a combination of the foregoing.

Step (II): Step of Causing Reaction Between Blocking Agent and Polyisocyanate Having Polyol Skeleton Obtained by Step (I)

This step is a step of causing a reaction between a blocking agent and the polyisocyanate having a polyol skeleton obtained by the step (I). This provides the blocked isocyanate (a3) having a branched structure according to this embodiment.

This blocking agent is a compound that reacts with isocyanate groups (—NCO) of diisocyanate to protect active isocyanate groups. The isocyanate groups protected with the blocking agent are referred to as blocked isocyanate groups or isocyanate groups blocked. The blocked isocyanate groups are protected with the blocking agent and hence remain stable in an ordinary state.

Heating the blocked isocyanate compound having blocked isocyanate groups causes the blocking agent to leave (be deblocked) from the blocked isocyanate groups, to provide the original isocyanate groups.

The blocking agent used in this step is not particularly limited as long as it is a (meth)acrylic compound having an amino group, but is preferably a compound selected from tert-butylaminoethyl (meth)acrylate, tert-pentylaminoethyl (meth)acrylate, tert-hexylaminoethyl (meth)acrylate, and tert-butylaminopropyl (meth)acrylate. This enables a decrease in the deblocking temperature of the blocked isocyanate.

This step is preferably performed such that the blocking agent and the diisocyanate having a polyol skeleton react in a solvent. The solvent is not particularly limited as long as the blocking agent and the polyisocyanate having a polyol skeleton dissolve therein. Specific examples of the solvent include those described in the explanations of the step (I).

This step is preferably performed in an inert atmosphere such as nitrogen, helium, or argon. This step is preferably performed at 0° C. or more and 150° C. or less, more preferably performed at 30° C. or more and 120° C. or less. In order to obtain the blocked isocyanate (a3) having a branched structure, the treatment is particularly preferably performed at 60° C. or more and 100° C. or less. This step may be performed under reflux. When this step is performed at a reaction temperature of less than 0° C., the reaction is less likely to proceed. When this step is performed at a reaction temperature higher than 150° C., the blocking agent itself may be polymerized through a polymerization reaction of (meth)acryloyl groups.

This step may be performed in the presence of a catalyst. Specific examples of the catalyst include those described in the explanations of the step (I).

In this step, in order to suppress the polymerization reaction of the (meth)acryloyl group of the blocking agent, a polymerization inhibitor may be used. Specific examples include benzoquinone, hydroquinone, catechol, diphenylbenzoquinone, hydroquinone monomethyl ether, naphthoquinone, t-butylcatechol, t-butylphenol, dimethyl-t-butylphenol, t-butylcresol, dibutylhydroxytoluene, and phenothiazine.

The blocked isocyanate obtained by this step can be isolated and purified by the same process as in the step (I).

To the blocked isocyanate (a3) having a side chain structure, the photo-radical generator (b), the polyrotaxane (c), and the chain extender (d) described in the second embodiment are added to obtain a photo-curable composition. When the polyrotaxane (c) has a hydroxyl group, the reaction accelerator (e) as in the second embodiment may be added.

When the photo-curable composition according to this embodiment is used to produce a three-dimensional article, the same forming method as in the first or second embodiment may be employed.

In the three-dimensional article produced in this way from the photo-curable composition according to this embodiment, due to the effect of polyrotaxane, in the case of application of an external stress or the like, crosslinking points move in accordance with the stress. Thus, in response to the stress, the tension among the polymers becomes uniform. As a result, the cured product has higher toughness than in the existing photo-curable compositions. The photo-curable composition according to this embodiment includes the blocked isocyanate (a3). As described in the formula (3) above, the blocked isocyanate (a3) may have a polycarbonate structure including a plurality of carbonate groups (—O—(C=O)—O—) in the molecular structure. Thus, when the cured product obtained by photo-curing and subsequently heat-treating the photo-curable composition according to this embodiment includes the polycarbonate structure therein, the photo-curable composition according to this embodiment enables stereolithographic forming of a three-dimensional article having high tensile strength and a high elastic modulus.

Applications

The three-dimensional-forming photo-curable compositions and their cured products according to the first to third embodiments are usable in, but not particularly limited, various applications such as resins for stereolithography 3D printers, sports goods, medical supplies and nursing care goods, industrial machinery and equipment, precision machinery, electric and electronic machinery, electric and electronic components, and building material goods.

EXAMPLES

Hereinafter, the present invention will be described in detail with reference to Examples. However, the present invention is not limited to these Examples. In Examples and Comparative Examples, identification of compounds and monitoring of reaction were performed in the following manner.

(1) Identification of Compounds

A sample (15 mg) was dissolved in 1.1 g of deuterated chloroform ($CDCl_3$), and subjected to $^1$H-NMR measurement using a nuclear magnetic resonance spectrometer JNM-ECA-400 (manufactured by JEOL Ltd.).

(2) Monitoring of Reaction (Confirmation of Disappearance of Isocyanate Groups)

A sample was measured using a Fourier transform infrared spectrometer (Spectrum One, manufactured by PerkinElmer, Inc.) by ATR (attenuated total reflectance). With the ordinate axis indicating absorbance, the presence or absence of a peak derived from isocyanate groups at or about 2260 $cm^{-1}$ was determined.

Synthesis Example 1: Synthesis of Blocked Isocyanate 1

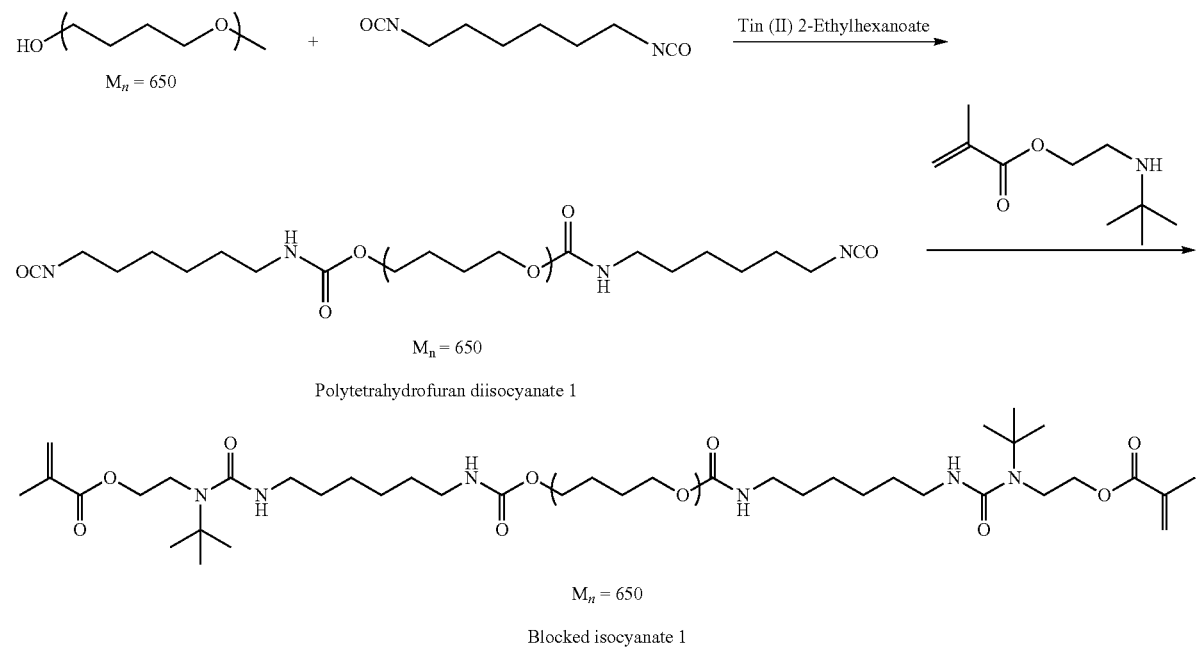

A blocked isocyanate 1 was synthesized in accordance with the above-described scheme. To a 500-mL reaction vessel, under an argon atmosphere, at room temperature, polytetrahydrofuran ($M_n$=650) (100 g, 154 mmol, 1.0 eq.) and hexamethylene diisocyanate (207 g, 1.23 mol, 1.0 eq.) were added and stirred. To this solution, tin(II) 2-ethylhexanoate (80 μL, cat.) was added. This solution was heated to 50° C., and, at the same temperature, stirred for 5 hours. This solution was left to cool to room temperature, and subsequently added to vigorously stirred hexane (4 L). This solution was stirred for another 15 minutes, and subsequently left to stand for 15 minutes; the upper layer (hexane layer) was removed by decantation. These procedures were further repeated twice to concentrate the lower layer (intermediate layer), to obtain 170 g of polytetrahydrofuran diisocyanate 1.

To the obtained polytetrahydrofuran diisocyanate 1, 300 mL of dichloromethane was added and ice-cooled under stirring. To this, hydroquinone (10 mg) and 2-(t-butylamino) ethyl methacrylate (142 g, 769 mmol, 5.0 eq.) were slowly added, and stirred at room temperature for 12 hours. This solution was analyzed by infrared spectroscopy. The above-described method was used to confirm the absence of the isocyanate-derived absorption peak.

Subsequently, the above-described solution was slowly added to vigorously stirred hexane (4 L), further stirred for 20 minutes, subsequently left to stand for 20 minutes, and the upper layer, namely, the hexane layer was removed by decantation. These procedures were further repeated three times; the target, namely, the lower layer was filtered through Celite, and subsequently concentrated in a high vacuum to obtain a colorless viscous liquid, namely, a blocked isocyanate 1 (184 g).

Synthesis Example 2: Synthesis of Blocked Isocyanate 2

A blocked isocyanate 2 was synthesized in accordance with the above-described scheme. To a 500-mL reaction vessel, under an argon atmosphere, at room temperature, polytetrahydrofuran ($M_n$=650) (80 g, 123 mmol, 1.0 eq.) and 4,4'-methylenebis(cyclohexyl diisocyanate) (323 g, 1.23 mol, 1.0 eq.) were added and stirred. To this solution, tin(II) 2-ethylhexanoate (80 μL, cat.) was added. This solution was heated to 50° C. and, at the same temperature, stirred for 5 hours. This solution was left to cool to room temperature, and subsequently added to vigorously stirred hexane (4 L). This solution was stirred for another 15 minutes, and subsequently left to stand for 15 minutes; the upper layer (hexane layer) was removed by decantation. These procedures were further repeated twice to concentrate the lower layer (intermediate layer), to obtain 126 g of a polytetrahydrofuran diisocyanate 2.

To the obtained polytetrahydrofuran diisocyanate 2, 300 mL of dichloromethane was added, and ice-cooled under stirring. To this, hydroquinone (10 mg) and 2-(t-butylamino) ethyl methacrylate (114 g, 615 mmol, 5.0 eq.) were slowly added, and stirred at room temperature for 1.5 days. This solution was analyzed by infrared spectroscopy. The above-described method was used to confirm the absence of the isocyanate-derived absorption peak.

Subsequently, the above-described solution was slowly added to vigorously stirred hexane (4 L), further stirred for 20 minutes, subsequently left to stand for 20 minutes, and

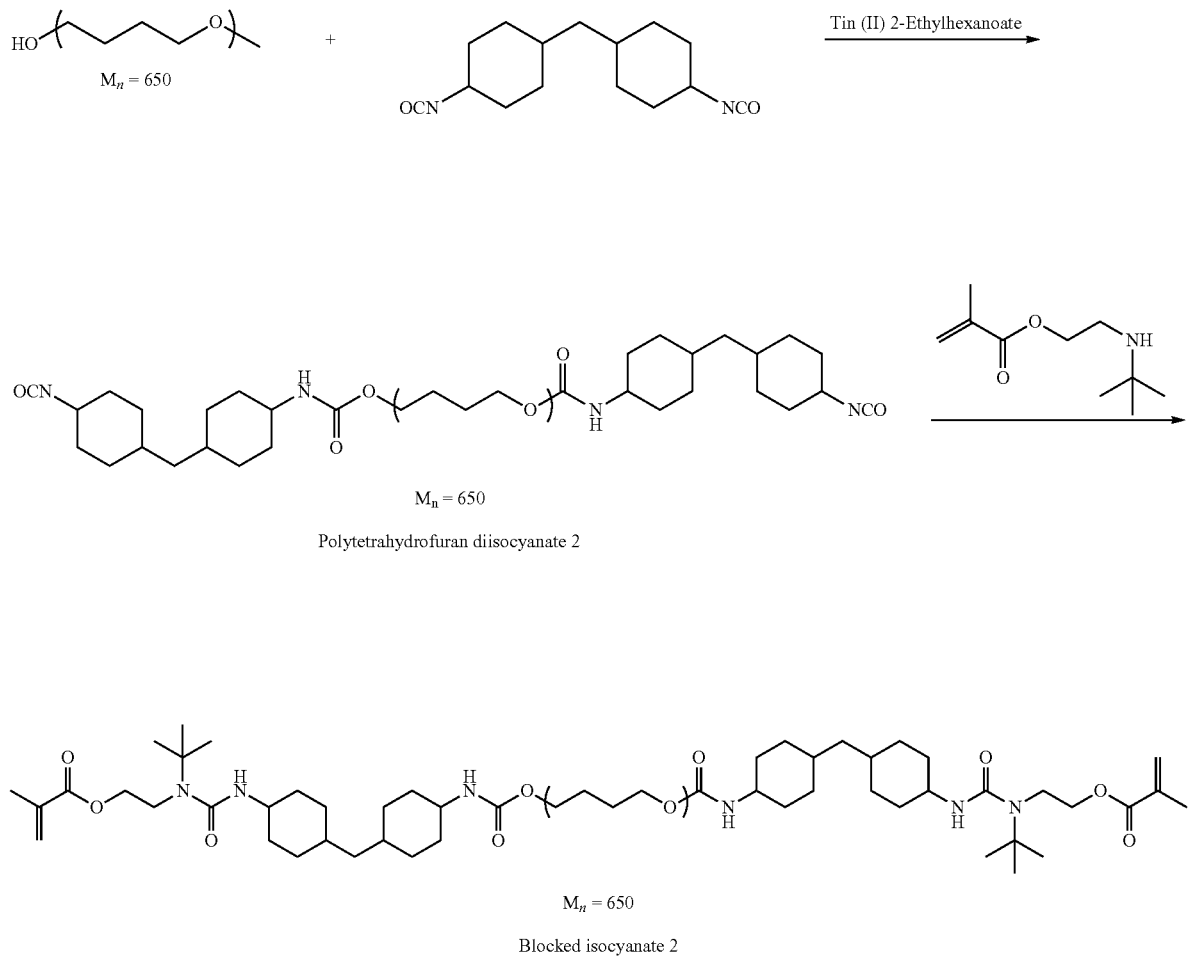

$M_n$ = 650

Polytetrahydrofuran diisocyanate 2

$M_n$ = 650

Blocked isocyanate 2 the upper layer, namely, the hexane layer was removed by decantation. These procedures were further repeated three times; the target, namely, the lower layer was filtered through Celite, and subsequently concentrated in a high vacuum to obtain a colorless viscous liquid, namely, a blocked isocyanate 2 (124 g).

Synthesis Example 3: Synthesis of Blocked Isocyanate 3

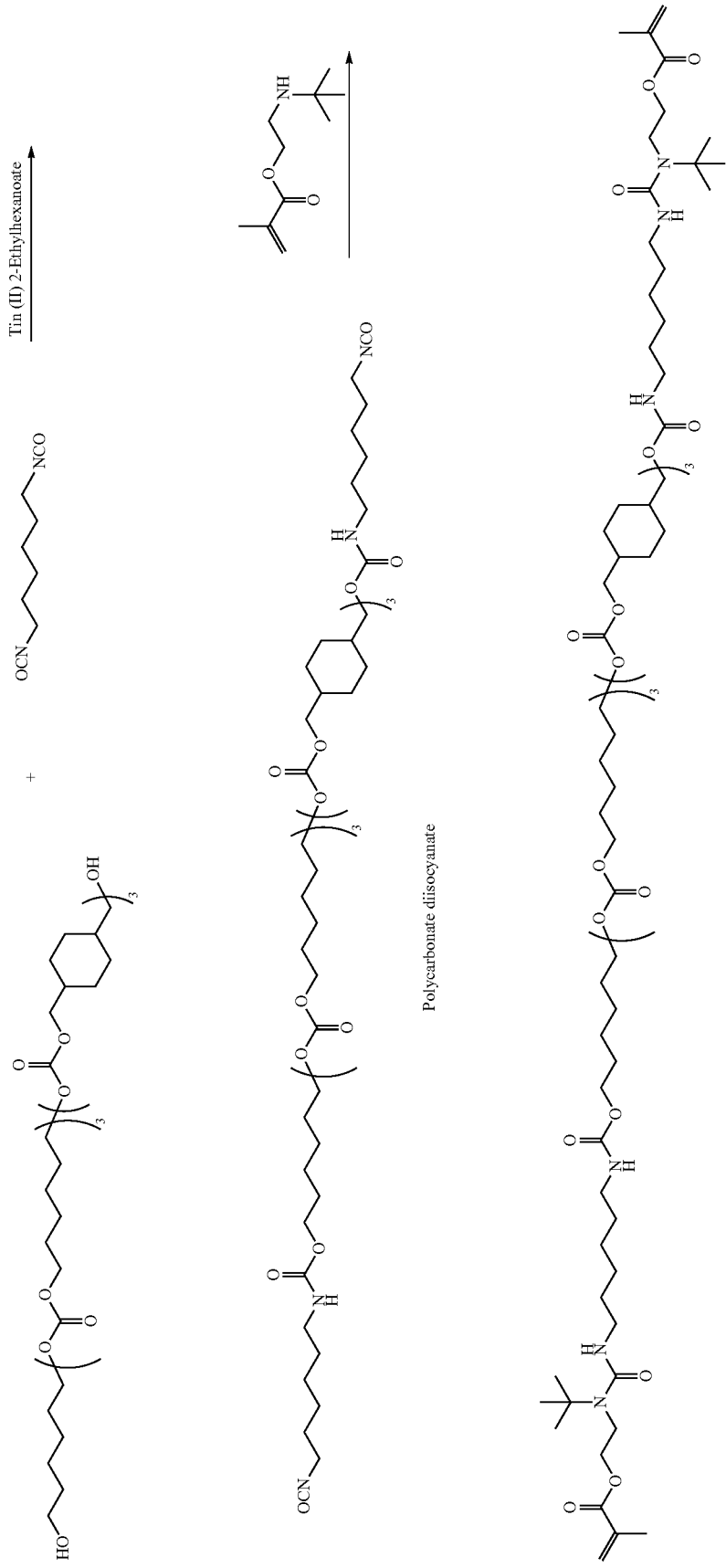

A blocked isocyanate 3 was synthesized in accordance with the above-described scheme. To a 300-mL reaction vessel, under an argon atmosphere, at room temperature, hexamethylene diisocyanate (168 g, 0.1 mol, 10 eq.), polycarbonatediol (eternacoll um-90 1/1) (90 g, 0.1 mol, 1.0 eq. (calculated on the basis of $M_n$=900)), and tin(II) 2-ethylhexanoate (70 µL, cat.) were added. This solution was heated to 50° C. and, at the same temperature, stirred for 3 hours; and subsequently the warm solution was slowly dropped to vigorously stirred hexane (3 L). This solution was further stirred for 20 minutes, subsequently left to precipitate; and the upper layer, namely, the hexane layer was removed. These washing procedures using hexane were further repeated twice. Subsequently, the obtained viscous liquid was concentrated under a high vacuum, to obtain a colorless viscous liquid, namely, polycarbonate diisocyanate (151 g).

To the obtained polycarbonate diisocyanate, dichloromethane (300 mL) and hydroquinone (20 mg) were added. To the resultant solution maintained at 5° C. using a cooling bath, 2-(t-butylamino)ethyl methacrylate (92.6 g, 0.5 mol, 5.0 eq.) was slowly dropped. Subsequently, the cooling bath was removed, and the solution was stirred at room temperature for 14 hours. This solution was analyzed by infrared spectroscopy. The above-described method was used to confirm disappearance of the isocyanate-derived absorption peak.

Subsequently, to vigorously stirred hexane (3 L), the above-described solution was slowly dropped. After completion of the dropping, the mixture was stirred for 30 minutes, and left to stand. Subsequently, the upper layer, namely, the hexane layer was removed by decantation, and the same procedures were again performed. The obtained viscous liquid was dried in a high vacuum at 40° C. for 6 hours, to obtain a colorless, highly viscous liquid, namely, a blocked isocyanate 3 (215 g).

Synthesis Example 4: Synthesis of Blocked Isocyanate 4

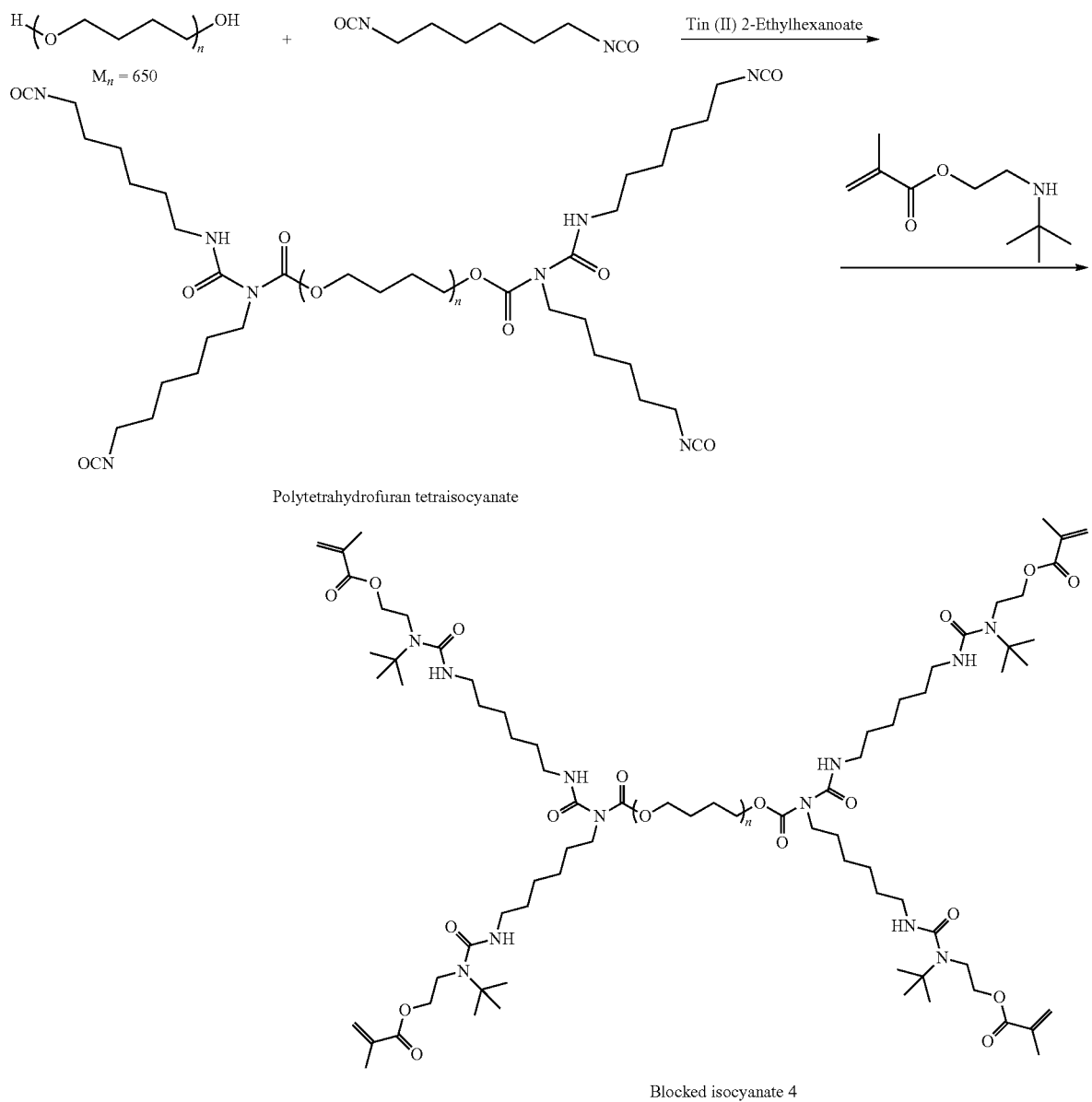

Blocked isocyanate 4

A blocked isocyanate 4 was synthesized in accordance with the above-described scheme. To a 500-mL reaction vessel, under an argon atmosphere, at room temperature, polytetrahydrofuran (100 g, 154 mmol, 1.0 eq.) having a number-average molecular weight $M_n$ of 650 and hexamethylene diisocyanate (207 g, 1.23 mol, 8.0 eq.) were added and stirred. To this solution, tin(II) 2-ethylhexanoate (80 μL, cat.) was added. This solution was heated to 80° C. and, at the same temperature, stirred for 8 hours. This solution was left to cool to room temperature, and subsequently added to vigorously stirred hexane (4 L). This solution was stirred for another 15 minutes, and subsequently left to stand for 15 minutes; the upper layer (hexane layer) was removed by decantation. These procedures were further repeated twice, and the lower layer was concentrated, to obtain 170 g of polytetrahydrofuran tetraisocyanate.

To the obtained polytetrahydrofuran tetraisocyanate, 300 mL of dichloromethane was added, and ice-cooled under stirring. To this, hydroquinone (10 mg) and 2-(t-butylamino) ethyl methacrylate (227 g, 1.23 mol, 8.0 eq.) were slowly added, and stirred at room temperature for 12 hours. This solution was analyzed by infrared spectroscopy. The above-described method was used to confirm the absence of the isocyanate-derived absorption peak.

Subsequently, to vigorously stirred hexane (4 L), the above-described solution was slowly added, further stirred for 20 minutes, subsequently left to stand for 20 minutes, and the upper layer, namely, the hexane layer was removed by decantation. These procedures were further repeated three times; the target, namely, the lower layer was filtered through Celite, and concentrated in a high vacuum to obtain a colorless viscous liquid, namely, a blocked isocyanate 4 (184 g).

Example 1

A photo-curable composition A was prepared in accordance with the following formulation.
Polymerizable Compound (a):
    <a-1> Isobornyl methacrylate 39.7 mass %
    <a-2> Blocked isocyanate 1 53.3 mass %
Photo-Radical Generator (b):
    <b-1> Bis(2,4,6-trimethylbenzoyl)-phenylphosphine oxide 0.7 mass %
Chain Extender (d):
    <d-1> 4,4'-Methylene-bis(cyclohexylamine) 6.3 mass %

Subsequently, in accordance with the following formulation, a three-dimensional-forming photo-curable composition 1 of Example 1 was prepared. Photo-curable composition A 90 mass %
Polyrotaxane (c):
    <c-1> SeRM SA2400C (manufactured by Advanced Softmaterials Inc.) 10.0 mass %

Comparative Example 1

A three-dimensional-forming photo-curable composition 2 of Comparative Example 1 was prepared as in Example 1 except that the polyrotaxane (c) in Example 1 was not used. In other words, the component formulation of the three-dimensional-forming photo-curable composition 2 of Comparative Example 1 is the same as the component formulation of the photo-curable composition A of Example 1.

Example 2

A photo-curable composition B was prepared in accordance with the following formulation.
Polymerizable Compound (a):
    <a-1> Isobornyl methacrylate 39.7 mass %
    <a-3> Blocked isocyanate 2 53.3 mass % Photo-radical generator (b): Bis(2,4,6-trimethylbenzoyl)-phenylphosphine oxide 0.7 mass %
Chain Extender (d): 4,4'-Diaminodiphenylmethane 6.3 mass %

Subsequently, in accordance with the following formulation, a three-dimensional-forming photo-curable composition 3 of Example 2 was prepared. Photo-curable composition B 90 mass %
Polyrotaxane (c):
    <c-1> SeRM SA2400C (manufactured by Advanced Softmaterials Inc.) 10.0 mass %

Comparative Example 2

A three-dimensional-forming photo-curable composition 4 of Comparative Example 2 was prepared as in Example 2 except that the polyrotaxane (c) in Example 2 was not used. In other words, the component formulation of the three-dimensional-forming photo-curable composition 4 of Comparative Example 2 is the same as the component formulation of the photo-curable composition B of Example 2.

Example 3

A photo-curable composition C was prepared in accordance with the following formulation.
Polymerizable Compound (a):
    <a-1> Isobornyl methacrylate 39.7 mass %
    <a-4> Blocked isocyanate 3 53.3 mass %
Photo-Radical Generator (b):
    <b-1> Bis(2,4,6-trimethylbenzoyl)-phenylphosphine oxide 0.7 mass %
Chain Extender (d):
    <d-1> 4,4'-Diaminodiphenylmethane 6.3 mass %

Subsequently, in accordance with the following formulation, a three-dimensional-forming photo-curable composition 5 of Example 3 was prepared. Photo-curable composition C 90 mass %
Polyrotaxane (c):
    <c-1> SeRM SA2400C (manufactured by Advanced Softmaterials Inc.) 10.0 mass %

Comparative Example 3

A three-dimensional-forming photo-curable composition 6 of Comparative Example 3 was prepared as in Example 3 except that the polyrotaxane (c) in Example 3 was not used. In other words, the component formulation of the three-dimensional-forming photo-curable composition 6 of Comparative Example 3 is the same as the component formulation of the photo-curable composition C of Example 3.

Example 4

A photo-curable composition D was prepared in accordance with the following formulation.
Polymerizable Compound (a):
    <a-1> Isobornyl methacrylate 39.1 mass %
    <a-4> Blocked isocyanate 1 49.7 mass % Photo-radical generator (b):
    <b-1> Bis(2,4,6-trimethylbenzoyl)-phenylphosphine oxide 0.6 mass %

<Reaction Accelerator> Dibutyltin dilaurate 0.6 mass %

Subsequently, in accordance with the following formulation, a three-dimensional-forming photo-curable composition 7 of Example 4 was prepared. Photo-curable composition D 90 mass %
Polyrotaxane (c):
<c-2> SeRM SH1310P (manufactured by Advanced Softmaterials Inc.) 10.0 mass %

Comparative Example 4

A three-dimensional-forming photo-curable composition 8 of Comparative Example 4 was prepared as in Example 4 except that the reaction accelerator in Example 4 was not used. In other words, the component formulation of the three-dimensional-forming photo-curable composition 8 of Comparative Example 4 is the same as the component formulation of the photo-curable composition C of Example 4.

Example 5

A photo-curable composition E was prepared in accordance with the following formulation.
Polymerizable Compound (a):
<a-1> Isobornyl methacrylate 35.7 mass %
<a-5> Branched blocked isocyanate 4 48.0 mass % Photoradical generator (b):

<b-1> Bis(2,4,6-trimethylbenzoyl)-phenylphosphine oxide 0.6 mass %
Chain Extender (d):
<d-1>4,4'-Diaminodiphenylmethane 5.7 mass %

Subsequently, in accordance with the following formulation, a three-dimensional-forming photo-curable composition 9 of Example 5 was prepared. Photo-curable composition C 90 mass %
Polyrotaxane (c):
<c-1> SeRM SA2400C (manufactured by Advanced Softmaterials Inc.) 10.0 mass %

Evaluation of Performance of Three-Dimensional-Forming Photo-Curable Compositions The three-dimensional-forming photo-curable compositions 1 to 6 prepared were used to produce cured products in the following manner. Between two quartz glass plates, a 300 μm spacer was interposed. Into the 300 μm width gap, such a photo-curable composition was poured. The poured photo-curable composition was irradiated with, using an UV irradiator (manufactured by HOYA-SCHOTT CORPORATION, trade name: "UV LIGHT SOURCE EX250"), ultraviolet rays at 7 mW/cm$^2$ for 120 seconds (total energy: 840 mJ/cm$^2$), to obtain a photo-cured product.

The obtained photo-cured product was placed in a heating oven at 125° C. and heat-treated for 4 hours, to obtain a photo- and heat-cured product.

Subsequently, from the obtained photo- and heat-cured product having a thickness of about 300 μm, a specimen was blanked out so as to have the No. 8 dumbbell shape. This specimen was measured in accordance with JIS K 7127 using a tensile tester (trade name: "STROGRAPH EII", manufactured by Toyo Seiki Seisaku-sho, Ltd.) at a test temperature of 23° C. and at a tensile speed of 10 mm/min, to measure the tensile elastic modulus, maximum load strength, and elongation. From the area surrounded by a stress-strain curve obtained in this tensile test, breakage energy was determined. The tensile elastic modulus is used as the index of rigidity. The maximum load strength is used as the index of strength. The breakage energy is used as the index of toughness.

The component formulations of the three-dimensional-forming photo-curable compositions, and mechanical characteristics of photo- and heat-cured products produced from the three-dimensional-forming photo-curable compositions are summarized in Table 1.

TABLE 1

| | | Example 1 | Comparative Example 1 | Example 2 | Comparative Example 2 | Example 3 | Comparative Example 3 | Example 4 | Comparative Example 4 | Example 5 |
|---|---|---|---|---|---|---|---|---|---|---|
| Polymerizable compound (a) | <a-1> | 35.7 | 39.7 | 35.7 | 39.7 | 35.7 | 39.7 | 39.1 | 39.3 | 35.7 |
| | <a-2> | 48.0 | 53.3 | — | — | — | — | 49.7 | 50.0 | — |
| | <a-3> | — | — | 48.0 | 53.3 | — | — | — | — | — |
| | <a-4> | — | — | — | — | 48.0 | 53.3 | — | — | — |
| | <a-5> | — | — | — | — | — | — | — | — | 48.0 |
| Photo-radical generator (b) | <b-1> | 0.6 | 0.7 | 0.6 | 0.7 | 0.6 | 0.7 | 0.6 | 0.7 | 0.6 |
| Polyrotaxane (c) | <c-1> | 10.0 | — | 10.0 | — | 10.0 | — | — | — | 10 |
| | <c-2> | — | — | — | — | — | — | 10 | 10 | — |
| Chain extender (d) | <d-1> | 5.7 | 6.3 | 5.7 | 6.3 | 5.7 | 6.3 | — | — | 5.7 |
| Reaction accelerator | | — | — | — | — | — | — | 0.6 | — | — |
| Elastic modulus [GPa] | | 1.07 | 1.03 | 1.28 | 1.24 | 1.08 | Unmeasurable (broken at the instant of gripping by chucks) | 0.39 | 0.61 | 1.01 |
| Maximum load strength [MPa] | | 39.9 | 37.5 | 49.2 | 53.8 | 39.7 | | 49.8 | 39.1 | 36.8 |
| Elongation [%] | | 110 | 78 | 37 | 8 | 108 | | 295.9 | 132.0 | 105 |
| Breakage energy [J/mm$^2$] | | 0.69 | 0.44 | 0.27 | 0.06 | 0.73 | | 1.74 | 0.72 | 0.78 |

Discussion of Results

In Table 1, comparison between Comparative Example 1 and Example 1, comparison between Comparative Example 2 and Example 2, and comparison between Comparative Example 3 and Example 3 have revealed the following: including the polyrotaxane (c) having a (meth)acryloyl group enables, without a decrease in the elastic modulus or maximum load strength, an increase in the breakage energy. In other words, the present invention enables, while maintaining high rigidity (elastic modulus) and high strength (maximum load strength), an increase in the toughness (breakage energy). In the case of using the blocked polyurethane, comparison between Example 4 and Comparative Example 1 has revealed the following: including the polyrotaxane having a hydroxyl group enables an increase in the breakage energy. Comparison between Example 4 and Comparative Example 4 has revealed the following: in the case of using the polyrotaxane having a hydroxyl group, addition of the reaction accelerator provides higher toughness (breakage energy).

Compared with Comparative Example 1, Example 5 in which the polyrotaxane is included in the blocked isocyanate having a branched chain structure, enables, while maintaining a high elastic modulus, an increase in the toughness (breakage energy).

A three-dimensional-forming photo-curable composition according to an aspect of the present invention provides a three-dimensional-forming photo-curable composition that enables formation of a three-dimensional article having higher toughness than before.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A three-dimensional-forming photo-curable composition comprising a (meth)acrylic compound having a (meth)acryloyl group; a photo-radical generator; and
   a polyrotaxane having a plurality of cyclic molecules having at least one of a (meth)acryloyl group and a hydroxyl group,
   wherein the (meth)acrylic compound includes a blocked isocyanate represented by a general formula (1) below:

A-B—C      (1)

(in the formula (1), A and C each independently represent a group represented by a formula (2) below, and B represents a group represented by a formula (3) below:

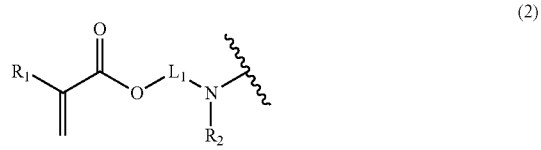      (2)

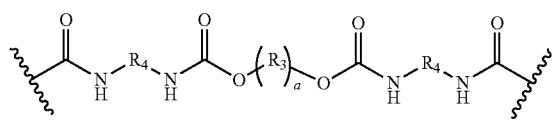      (3)

(in the formula (2), $R_1$ represents a hydrogen atom or a methyl group, $R_2$ represents a hydrocarbon group that has 1 to 10 carbon atoms and may have a substituent, and $L_1$ represents a divalent hydrocarbon group that has 1 to 10 carbon atoms and may have a substituent; in the formula (3), $R_3$ and $R_4$ each represent a hydrocarbon group that has 1 to 20 carbon atoms and may have a substituent, and a is an integer of 1 or more and 100 or less),
   wherein the polyrotaxane has a hydroxyl group, and the three-dimensional-forming photo-curable composition comprises a reaction accelerator.

2. The three-dimensional-forming photo-curable composition according to claim 1, wherein, in the formula (3), $R_3$ has at least one divalent linking group selected from the group consisting of formulas (A-1) to (A-4) below:

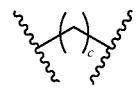      (A-1)

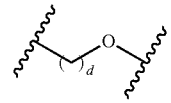      (A-2)

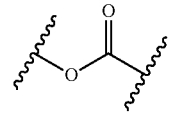      (A-3)

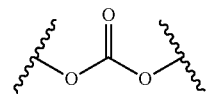      (A-4)

(in the formula (A-1), c is an integer of 1 or more and 10 or less; and, in the formula (A-2), d is an integer of 1 or more and 10 or less).

3. The three-dimensional-forming photo-curable composition according to claim 1, wherein the blocked isocyanate is represented by a general formula (4) below:

A-B-A      (4).

4. The three-dimensional-forming photo-curable composition according to claim 1, further comprising a radical polymerizable compound other than the (meth)acrylic compound and/or a cationic polymerizable compound.

5. The three-dimensional-forming photo-curable composition according to claim 1, wherein an amount of the polyrotaxane added relative to 100 mass % of a total amount of the photo-curable composition is 1 mass % or more and 50 mass % or less.

6. The three-dimensional-forming photo-curable composition according to claim 1, wherein an amount of the photo-radical generator added relative to 100 mass % of a total amount of the photo-curable composition is 0.05 mass % or more and 20 mass % or less.

7. A method for producing a three-dimensional article, comprising a step of photo-curing a three-dimensional-forming photo-curable composition based on slice data to form a formed article,
   wherein the three-dimensional-forming photo-curable composition is the three-dimensional-forming photo-curable composition according to claim 1.

8. A method for producing a three-dimensional article, comprising a step of photo-curing a three-dimensional-forming photo-curable composition based on slice data to form a formed article; and
   a step of heat-treating the formed article to obtain a three-dimensional article,
   wherein the three-dimensional-forming photo-curable composition is the three-dimensional-forming photo-curable composition according to claim 1.

* * * * *